United States Patent
Kolstad et al.

[11] Patent Number: 5,859,270
[45] Date of Patent: Jan. 12, 1999

[54] METHOD FOR PREPARATION OF PURIFIED MONOGLYCERIDES; AND, PRODUCTS

[75] Inventors: Jeffrey John Kolstad, Wayzata; Richard D. Benson, Long Lake; Scott D. Bloomer, Eden Prairie; Paris Tsobanakis, Inver Grove Heights, all of Minn.

[73] Assignee: Cargill, Incorporated, Minneapolis, Minn.

[21] Appl. No.: 614,468

[22] Filed: Mar. 13, 1996

[51] Int. Cl.$^6$ ........................... C11B 3/00
[52] U.S. Cl. .................. 554/204; 554/206; 554/207; 554/195
[58] Field of Search .................. 554/204, 206, 554/207, 175

[56] References Cited

U.S. PATENT DOCUMENTS

| | | | |
|---|---|---|---|
| 2,651,646 | 9/1953 | Goldsmith et al. | 260/410.7 |
| 2,682,550 | 6/1954 | Young et al. | 260/410.7 |
| 2,727,913 | 12/1955 | Kuhrt et al. | 260/410.7 |
| 2,740,799 | 4/1956 | Houng et al. | 260/410.7 |
| 2,759,954 | 8/1956 | Miller et al. | 260/410.7 |
| 3,097,098 | 7/1963 | Allen et al. | 99/123 |
| 3,669,848 | 6/1972 | Selden | 203/94 |
| 5,434,280 | 7/1995 | Peter et al. | 554/205 |

OTHER PUBLICATIONS

Feuge, R.O. and Gros, Audrey T., "Modification of Vetetable Oils. IX. Purification of Technical Monoglycerides", J. Amer. Oil Chem. Soc., vol. 27, pp. 117–122, Apr. 1950.

Monick, J.A. and Treybal, R.E., "Separation of Monoglycerides, Diglycerides, and Triglycerides by Liquid–Liquid Extraction", J. Am. Oil Chem. Soc., vol. 33:193–197 (May 1956).

Zilch, K.T. and Dutton, H.J., "Analysis of Fat Acid Oxidation Product by Countercurrent Distribution Methods", Analytical Chemistrictry, vol. 23, No. 5, 775–778 (May 1951).

*Primary Examiner*—Gary Geist
*Assistant Examiner*—Deborah D. Carr
*Attorney, Agent, or Firm*—Merchant, Gould, Smith, Edell, Welter & Schmidt, P.A.

[57] ABSTRACT

A method of preparing a purified monoester composition is provided. The method generally involves a step of adding triglycerides to the crude monoester composition, with a follow up step of extracting into an alcohol/water phase, of the monoester to be purified. The process can be utilized to isolate and purify monoglycerides and propylene glycol monoesters, to advantage. The invention also concerns equipment for conduct of the processes, provision of preferred food additives, and provision of preferred food industry compositions.

29 Claims, 1 Drawing Sheet

METHOD FOR PREPARATION OF PURIFIED MONOGLYCERIDES; AND, PRODUCTS

FIELD OF THE INVENTION

The present invention relates to monoester production and isolation. In one type of application, it particularly concerns methods of isolating purified monoglycerides from crude monoglyceride mixtures. In preferred applications, liquid-liquid extraction is utilized to advantage. The techniques can also be applied to isolate related materials, such as propylene glycol monoesters.

BACKGROUND OF THE INVENTION

Monoesters such as monoglycerides are widely used food additives, for example as emulsifiers and dough conditioners. In general, such materials comprise esters of fatty acids. The term "monoglyceride" specifically refers to a derivative of glycerol, i.e. a glyceride, in which only one of the three available hydroxy groups of the glycerol moiety is esterified. By "esterified" in this context, it is meant that the glycerol moiety forms the alcohol residue of an ester (typically with a fatty acid residue).

In general, crude monoglyceride mixtures are made from reacting naturally occurring triglycerides, often obtained from oil seed processing, with glycerol. Such reactions generate a mixture of monoglycerides, diglycerides and triglycerides. Limitation on monoglyceride production, via this approach, is generally controlled by: (1) solubility of the glycerol in the reaction mixture; (2) the overall equilibria statistics; and, (3) time. Typical commercially available crude monoglyceride mixtures made using this approach include ratios of monoglyceride:diglyceride:triglyceride (by weight) of about 45:45:10; or about 60:35:5, depending on processing conditions used.

In many instances, it is preferred to utilize more purified monoglycerides. That is, crude monoglyceride compositions or mixtures are purified for at least partial isolation of the monoglycerides from the diglycerides and triglycerides. In general, monoglyceride distillation has been the most widely utilized technique for such purifications. Typically the crude monoglyceride mixture is distilled under vacuum, in a short path distillation process. The distillate generally comprises greater than 90% (by weight) monoglycerides. The remainder generally comprises diglyceride. During the process, the monoglycerides are generally heated to at least 200° C.

In other processes, supercritical extractions have been used for isolation of monoglycerides. These generally concern extraction under pressures greater than atmospheric (typically 30–80 atmospheres) and temperatures in excess of 100° C. (typically 110° C. or so). They generally concern extractions with low molecular weight hydrocarbons, such as propane. Such approaches are generally prohibitively expensive, for application on a large scale.

Closely related materials to monoglycerides include propylene glycol monoesters (PGME's). Such materials are generally made from esterifying propylene glycol with naturally occurring oils, i.e. fatty acid mixtures, resulting in a mixture of monoesters and diesters. Generally the monoesters are isolated by distillation. Such materials are also widely utilized as emulsifiers and as dough conditioners in the food industry.

SUMMARY OF THE INVENTION

According to the present invention, a method for preparing a purified monoester composition from a crude monoester composition is provided. The process is typically and preferably used to purify crude monoester compositions including $C_3$-diol or $C_3$-triol monoesters of fatty acids. The term "$C_3$-diol" in this context is meant to refer to a 3-carbon chain dihydroxy compound, typically wherein each hydroxy group is on a separate carbon. The term "$C_3$-triol" in this context is meant to refer to a 3-carbon chain trihydroxy compound, typically wherein each hydroxy group is on a separate carbon atom. Typically $C_3$-diol monoesters purified according to the present invention will comprise propylene glycol monoesters; and, $C_3$-triol monoesters purified according to the present invention will comprise monoglycerides.

Typically, crude monoester compositions to be purified according to the present invention will comprise crude monoester compositions made from reactions of naturally occurring triglycerides, such as palm oil, canola oil, soybean oil, sunflower seed oil, or beef tallow or various fats. The triol monoesters are typically prepared by reacting such naturally occurring oils or fats with glycerol; and, the $C_3$-diol crude monoester compositions are generally prepared by reacting naturally occurring triglycerides with propylene glycol. The term "naturally occurring" in this context and in connection with identifying oils or fats, is merely meant to refer to oils, fats or mixtures of oils and/or fats that can be isolated from natural products; for example from crops or animal processing. It is not meant that the materials are in their natural form, but indeed typically will have been isolated through some form of processing. Also, it is not meant by the term "naturally occurring" that the isolation could not have been from a man-made hybrid plant or animal, or genetically altered plant or animal.

It will also be understood that techniques according to the present invention can be utilized in association with oils/fats that have been modified from their natural form in some manner, for example through hydrogenation or various esterifications. Herein the term "oil" is differentiated from the term "fat" in that oils are generally liquid at room temperature and fats are generally solid or semi-solid at room temperature. Both are triglycerides and will generally be treated analogously in processes according to the present invention.

In general, the purification includes a step of adding, to the crude monoester composition to be purified, an effective amount of triglyceride(s) to form a primary extraction triglyceride-containing phase. In this context, the term "effective amount" is generally meant to refer to an amount of triglyceride(s) which will facilitate retention of diglyceride(s) in a "primary extraction triglyceride-containing phase" during the extraction. Typically and preferably the amount of triglyceride(s) addition will be about 30 to 200 parts by weight per 100 parts crude monoester, especially when the triglyceride(s) comprises the same triglyceride(s) (or is derived from the same triglyceride) as was used to form the crude monoester composition. Most typically 45 to 100 parts by weight per 100 parts crude monoester will be used.

Alternatively, one can characterize processes according to the present invention in terms of the composition of the mixture from which the monoglycerides are extracted. The mixture would generally comprise at least 30%, by weight, triglycerides, as a result of the triglyceride addition to the crude monoglyceride prior to extraction. In general, the composition would comprise a diglyceride content of no greater than about 2 times the monoglyceride content, by weight. This latter would also typically be true of the crude monoglycerides to be processed. Preferably, the mixture from which the extraction of monoglycerides occurs, has a diglyceride presence which is less than the triglyceride presence, by weight, generally as a result of the triglyceride additions to the crude monoglyceride mixture.

Typical, preferred, processes according to the present invention comprise a step of extracting the primary extraction triglyceride-containing phase with an alcohol/water extractant. Typically and preferably the alcohol is a low molecular weight ($C_3$ or less) alcohol. Preferably it is an alcohol of a straight chain hydrocarbon compound. Typically it is a monohydroxy compound, most preferably with a terminal —OH group. Most preferably it is ethanol. Most typically, especially when the alcohol is ethanol, the alcohol/water extraction will comprise, by weight, at least 60% alcohol and no more than about 90% alcohol. Also, typically it will contain 10–40%, by weight, water. Most typically it will include about 70–85% alcohol, and 15–30% water, by weight. Such systems will generally be quite selective, for extraction of monoesters from the crude monoester composition, with substantial selectivity relative to extraction of diesters or triesters. Such systems will also generally have a high extraction factor for monoesters, allowing use of relatively low extractant flow rates.

Preferably, after the step of separating, the alcohol/water extractant phase is treated for isolation of purified monoester composition therefrom. This will typically involve a step of removing the alcohol/water extractant from the extractant phase, for example by distillation of the alcohol/water. Preferably, regardless of the specific technique used, the step of isolating is conducted without a step of distilling the isolated monoester(s).

In certain preferred operations according to the present invention, the step of providing crude monoester compositions comprises providing crude monoglyceride compositions. Crude monoglyceride compositions typically contain at least 30% monoglyceride and at least 25% diglyceride, based on total weight of monoglycerides, diglycerides, and triglycerides therein. Typically they contain no more than about 70% monoglycerides, by weight, based on total weight of monoglycerides, diglycerides and triglycerides, and they are typically purified to provide a purified monoester composition having a monoglyceride presence of no less than 85%, based on total weight of monoglycerides, diglycerides and triglycerides in the purified monoester composition. Indeed, typically the purification processes will be practiced to achieve at least 90% monoglycerides, on such a basis, and in some preferred applications, they will be practiced to provide at least 95% by weight monoglycerides in the purified monoglyceride composition. When the practice is with monoesters other than monoglycerides, for example PGMEs, similar results can be obtained. However, typically with PGME's the compositions will also include some propylene glycol diesters, as well as monoglycerides, diglycerides and triglycerides from processing. In such instances, the purification will generally involve selectively retaining monoglyceride with the purified PGME, relative to diglyceride and triglyceride.

Preferably the step of extracting with alcohol/water extractant comprises conducting a multi-stage counter-current extraction; typically with at least two stages and preferably at least three. Preferably the extraction is conducted at a temperature of at least about 60°–80° C. and not greater than 120° C., so that triglycerides present will be in the liquid phase and the alcohol/water solvent will generate only relatively low pressures. Typically, the extraction with ethanol/water is conducted at about atmospheric pressure, and preferably at pressures no higher than 5 atmospheres.

Preferred processes according to the present invention include a step of back extracting or washing the alcohol/water extractant phase from the primary or first extraction. The step of back extracting or washing is preferably conducted with a triglyceride-containing phase, for further "tuning" of the purification, to reduce a presence of diglycerides that may have been extracted into the alcohol/water extractant, during the primary extraction. The step of back extracting or washing, then, can be referred to as a "wash" of the extractant from the primary extraction with a triglyceride-containing phase.

Preferably the triglyceride-containing phase, from the step of washing, is added to the crude monoglyceride mixture, as a source of added triglycerides for conduct of the primary extraction. Preferably the step of washing also comprises a multi-stage counter-current washing; again typically having at least two stages, preferably at least three.

According to some aspects and applications of the present invention food additives are provided. In general, the food additives comprise purified monoglyceride (or other monoester) component isolated or purified according to the present invention. In certain preferred systems, the purified monoglyceride (monoester) component comprises at least 85% by weight monoglycerides (or monoester), based on the total weight of monoglycerides (monoesters), diglycerides (diesters) and triglycerides (triesters) in the monoglyceride (monoester) component.

In general, preferably when crude monoglyceride compositions are utilized, prior to addition of the triglycerides thereto, the crude monoglyceride composition comprises, by weight, no more than 20% triglycerides, based on total weight of monoglycerides, diglycerides, and triglycerides in the crude monoester composition. Again, preferably it contains no more than about 70% monoglycerides, by weight, based on total weight of monoglycerides, diglycerides, and triglycerides in the crude monoglyceride composition. In general, the method can be characterized as being conducted to achieve the isolation of purified monoester composition, having: a monoglyceride presence of no less than 85%, based on total weight of monoglycerides, diglycerides and triglycerides in the purified monoester composition; and, a diglyceride-to-triglyceride weight ratio, in the purified monoester composition, of no greater than 1:1.

The present invention also concerns provision of a processing facility for purifying crude monoester compositions. The processing facility generally includes a primary counter-current extractor as described; a secondary counter-current extractor as described; fluid direction conduit arrangements for preferred cycling and direction of materials; and, a source of triglyceride and a source of crude monoglyceride (monoester) constructed and arranged as necessary, for provision of preferred operations.

DETAILED DESCRIPTION

Figure 1:
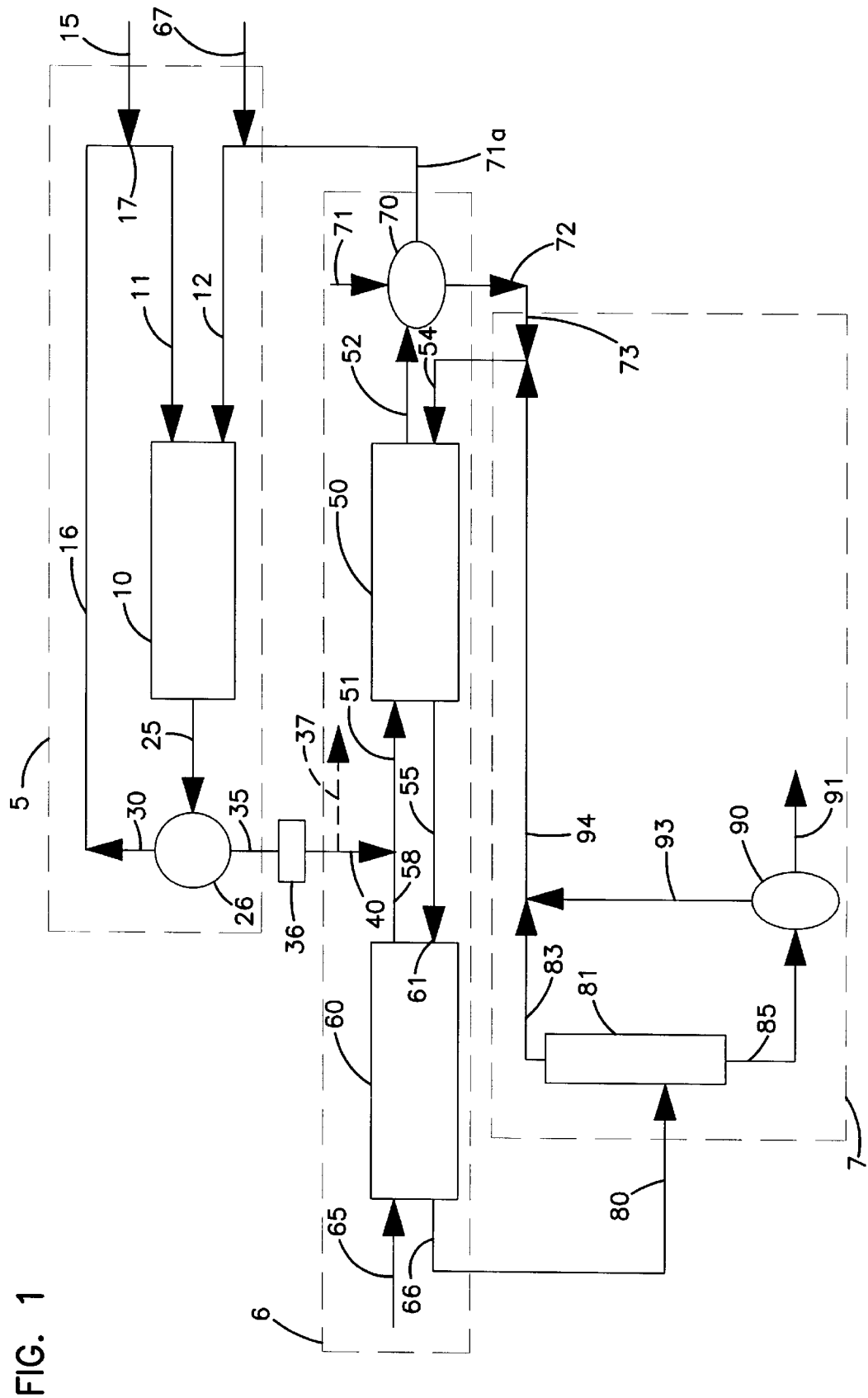
FIG. 1 is a schematic presentation of a process and equipment for practice of the process, according to the present invention.

The present invention concerns methods, techniques and equipment for purifying or isolating materials such as monoglycerides and propylene glycol monoesters, from mixtures containing related diesters and related triesters. The techniques described generally utilize preferred liquid-liquid extractions, to facilitate the process. Most preferred practices are conducted under conditions in which the monoester to be isolated is not distilled at any point in the process. Preferably it is conducted without subjecting the crude monoester composition, after formation, to temperatures in excess of 140° C. and/or pressures in excess of about 5 atm. Typically they will be practiced without subjecting the crude monester composition, after formation, to temperatures in excess of 120° C. and/or pressures in excess of 3 atm. Also, typically, (at least in most preferred applications) no large amounts of materials such as non-alcohol solvents (propane, butane, hexane, ethers, ketones etc.) are used, during the step of extracting monoglycerides from the crude mixtures. Preferably none of these materials is used. Herein the term "no large amounts" in this context is meant to refer to no more than about 15–20%, by weight, of the referenced solvent.

I. Materials Purified

Glycerol is a 1,2,3-trihydroxy propane, or propylene triol. It is typically obtained from hydrolysis or alcohol reaction, of naturally occurring triglycerides, during fatty acid production. Propylene glycol is a 1,2-dihydroxy propane (1,2-propane diol). Propylene glycol is typically obtained from hydrolysis of propylene oxide. Techniques according to the present invention were developed to facilitate isolation and purification of monoesters of such materials, from crude mixtures containing the monoesters and diesters (and in some instances triesters). The particular monoesters of greatest interest, are fatty acid monoesters, for example propylene glycol or glycerol monoesters of fatty acids. Herein the terms "isolation and purification" when utilized in this context, and in similar contexts, are not meant by themselves to specifically refer to some particular level of purity of the monoester, other than an improved purity relative to the crude mixture. However, in typical applications, the technique will be utilized to obtain purities of at least 85% (by weight), and usually preferably to obtain purities of at least 90%, relative to contaminating diesters and triesters. In some specific applications, purities of 95% or greater can be obtained.

It is foreseen that techniques according to the present invention can be utilized to isolate and purify a variety of monoesters, from crude mixtures of the monoesters with related di- (and/or tri-) esters. For example, according to the present invention, monoesters isolatable using the techniques typically comprise esters of $C_3$- or $C_4$-diols or triols, wherein each hydroxy group is on a separate, isolated carbon in the 3 or 4 carbon group. Typically, the applications will cover esters wherein the ester group is a straight chain $C_3$-multi-hydroxy compound. Typically the compounds will be monoesters of dihydroxy- or trihydroxy-substituted propane or butane.

Herein the term "fatty acid" is meant to refer to acids having at least 4 carbon atoms, typically, but not necessarily, 12 to 20 carbon atoms, and includes saturated and unsaturated fatty acids.

The fatty acids of greatest interest to the present invention are those derived from naturally occurring mixtures of oils or fats (or fatty acid derivatives) found in such fats and oils as: palm oil; soybean oil; canola oil; peanut oil; cottonseed oil; coconut oil; and, beef tallow. (The term "naturally occurring" in this context is meant to include reference to products from processing man-made hybrids or genetically altered plants or animals, as well as natural ones.) Such materials generally include mixtures of saturated and unsaturated fatty acid derivatives (fats) and primarily include fatty acid derivatives having an even number of carbons in the fatty acid backbone. They typically include predominately $C_{10}$ or greater acids, typically $C_{12}$ or greater. Herein when the term "$C_{10}$" is used in this context, it is meant that the carbon chain of the acid fragment, including the acid carbon, has 10 carbon atoms in it.

Reaction mixtures to be purified according to the present techniques can be made in a variety of manners. Typically they will comprise mixtures of mono-esters and di-esters, and in some instances tri-esters, of a short chain di-hydroxy or tri-hydroxy compound. A desired result of the purification, typically includes generation of a mixture comprising at least 85%, and typically at least 90%, by weight, monoester (relative to contaminating diester and, if present, triester), and more preferably at least 95% by weight, from a mixture comprising at least 30% and typically no more than about 70–80% (and sometimes no more than 60%) by weight of the monoester, typically about 35–65% by weight, based on total weight of monoester plus diester (and, if present, triester).

Although crude mixtures of monoesters to be purified according to the present invention may be obtained in a variety of manners, typically they comprise the reaction product of 3- or 4-carbon chain di- or tri-hydroxy compound, with naturally occurring fatty acid ester mixtures, typically triglycerides. Most typically, the crude mixtures will comprise the reaction product of either glycerol or propylene glycol with a naturally occurring triglyceride mixture such as palm oil, soybean oil, canola oil or sunflower oil. In some instances modified oils (such as partially hydrogenated oils or esterified oils) may be used.

Typical crude monoglyceride mixtures used in processes according to the present invention will include monoesters and diesters in a weight ratio of about 0.75:1 to about 2:1 (mono:di), and in some instances may include a minor percentage (for example, up to 10–15% by weight) of triester. Typical crude monoglyceride mixtures, which will be purified using techniques according to the present invention, comprise products having mono:di:triesters present in weight ratios of about 45:45:10 or about 60:35:5. These are the common crude monoglyceride mixtures, made in industry.

It is foreseen that crude monoglyceride mixtures containing variations from these amounts will be purifiable with techniques according to the present invention. However, the techniques were developed in a manner calculated to especially facilitate purification of such mixtures, because they are the types of mixtures prevalent in industry as crude monoglyceride mixtures.

When techniques according to the present invention are utilized for purification of monoesters such as propylene glycols, i.e. monoesters other than monoglycerides, generally analogous conditions and levels of purification to those described above with respect to monoglycerides are achievable. In such context, however, the weight percent of monoester stated will generally be based upon total weight of monoester, diester, and triester present, regardless, for example, of whether the diester and triester are glyceride esters or esters of the particular alcohol of concern, or a mixture of both. The latter will be typical, since, for example, propylene glycol monoesters are typically prepared from triglyceride and thus crude propylene glycol monoester mixtures will include propylene glycol diesters, monoglycerides, diglycerides and triglycerides.

II. Other Characterizations of Preferred Processing and Purity

A. Purity

In general, as explained above, techniques according to the present invention were generally developed to provide preferred overall levels of purity with respect to purified monoglycerides, in advantageous cost-effective manners. During the course of the study, however, it was discovered that while the absolute level of purity of the monoester was of great importance, it was not the only factor of interest with respect to preferred products. In particular, it was found that in some instances, preferred products were obtained if there was a focus at least in part upon the content of the principal contaminating esters.

For example, as indicated above, when the material to be purified is a crude monoglyceride mixture, the mixture generally comprises monoglycerides, diglycerides, and triglycerides. During the studies, it was found that preferred purifications would occur if, with respect to the contaminating diglycerides and triglycerides, the purification was conducted in such a manner that the diglyceride to triglyceride ratio, by weight, was reduced to no more than 1:1 (and typically less), and typically and preferably to less than 1:3. Since crude monoglyceride mixtures generally contain greater percentage of diglycerides than triglycerides, by weight, by the above, it is generally meant that the process should be conducted in such a way that focus is on diglyceride removal.

In the same context, and as part of the same evaluations, it was observed that in general preferred purified monoglycerides not only contain at least 85% (and preferably at least 90%) by weight monoglycerides, but also have a monoglyceride-to-diglyceride ratio, by weight, of at least 40:1 and preferably at least 70:1. Again, typically and preferably, the majority of the contaminants in the purified monoglycerides, by weight, in such systems is preferably triglyceride (as opposed to diglyceride).

B. Processing

As will be apparent from the following discussions and examples, a variety of techniques have been developed for characterizing preferred steps of processing. Some of the more significant are as follows:

1. Loading

In general, processes according to the present invention will not be considered preferred or particularly effective unless the loading of the monoester to be purified in the polar phase or extractant, is substantial. That is, with techniques according to the present invention, one is not only trying to obtain high selectivity during the extraction so that good purity results, but one is also seeking simultaneously a relatively high loading or at least substantial loading, so that the process is efficient. If loading is too low, the process will be commercially undesirable since high amounts of extractant would be needed. In typical preferred processes according to the present invention, including under the conditions described herein below, one can achieve loading of the monoester(s) in the extractant during the extracting process of at least 10 grams (g) per 100 g extractant, and typically loadings of at least 15 g per 100 g extractant (or more) are obtained. The term "10 g monoesters per 100 g" extractant refers to the load in the extractant phase leaving the extraction step, for example at line 55, FIG. 1.

2. Selectivity

Processing according to the present invention can be characterized with respect to the selectivity of the extraction. This can be phrased in a variety of ways including the extraction selectivity for the monoester over the diester; the extraction selectivity for the triester over the diester; and, the selectivity of extraction for the monoester over the triester, when the process includes purification of mixtures including monoesters, diesters, and triesters. A selectivity of particular concern will be the selectivity for the monoester over the diester.

In general, selectivity ($\alpha 1,2$ of component 1 to component 2) is defined by the ratio, for the extractant phase to the raffinate phase, of the ratio of concentrations, by weight, of component 1 to component 2. Thus, $\alpha$ is a ratio of ratios. From the examples given below, it will be understood that selectivities for monoester over diester of >5 and for monoester over triester of >50 can be readily obtained with processing according to the present invention.

III. Methods of Purification—Generally

A. Monoglyceride Purifications

In general, crude monoester mixtures, such as crude monoglyceride compositions, according to the present invention are purified through liquid-liquid extractions. More specifically, monoglyceride values in the crude mixture are preferentially extracted into (partitioned into) an alcohol-containing phase. The separation/purification is facilitated by the following:

1. Provision of sufficient water in the alcohol-containing phase to provide desirable selectivity of extraction; i.e. preferential extraction or partitioning of monoglycerides vs. diglycerides (or even triglycerides) into the alcohol phase; and 2. Provision in the non-alcohol phase of a component to facilitate solubility of diglycerides (and triglycerides) in that phase. Preferably this added component includes a triglyceride or a triglyceride mixture. Most preferably it is a naturally occurring food substance and does not contain substantial amounts (greater than 20% and preferably none) of non-functionalized organic solvent such as a hydrocarbon (propane, butane, etc.).

In general, purified monoglycerides, with monoester contents of greater than 90%, until now have been available commercially only as distilled monoglycerides. Because of the low vapor pressure, monoglycerides can be distilled only under relatively high vacuum and relatively high temperatures. This leads to a process which is rather expensive and which can lead to undesirable products. Unfortunately, distilled monoesters are also sometimes responsible for a bitter flavor in the finished product, limiting the level to which they can be added.

In most applications it is the monoester which is providing the desired functionality, with the attendant diester being present only as an unwanted byproduct. A source of more highly purified, low cost, monoesters can be, therefor, generally provided by the present invention.

In certain applications, the diester is in fact a detrimental component, and a higher price is paid in order to get the more highly purified, distilled monoester. In some instances, the presence of the diester is believed to modify the phase behavior of the monoester, interfering with functional activity.

It is true that some alternative purification processes have been contemplated in the art. Fractional crystallization, which utilizes differences in melting points between the monoesters and other components, is generally feasible only for products with narrowly defined fatty acid profiles, such as fully saturated oil of IV<2, where the fatty acids are dominated by a single species such as stearine. In this context the term "IV" refers to the iodine value, which is an indicator of the degree of saturation. Products with a range of IV will tend to fractionate by IV, rather than by degree of esterification.

Supercritical extraction using an extractant such as propane has been suggested as an approach to purification, but it is too expensive to be commercially viable. In general, it requires relatively high pressures (>60 atm) and involves relatively low loading (typically <5 wt % fat in the extractant wherein the term "fat" refers to whatever fatty acid ester is in the extractant.) It is noted that use of a non-polar extractant in supercritical extractant involves extraction of the di- and tri-esters away from the monoester, and into the extractant. Adsorption techniques, wherein the monoesters are adsorbed onto a solid support and are later desorbed into a solvent, may be feasible but typically would require large amounts of resin, which can increase cost.

Until now, the use of liquid extractants in a viable system has not been developed or proposed. For example, low boiling hydrocarbons such as hexane could be envisioned to selectively extract the di- and tri-esters, leaving the monoesters behind. In practice, however, the hydrocarbon has generally had too great a solvency and typically also extracted the monoglyceride, often forming a single phase system. A supercritical use of propane has been suggested as a method around these problems, but such an approach is impractical and is generally asserted to be prohibitively expensive. Alcohols or alcohol/water blends may also have been proposed to extract the monoesters, and leave the diesters and triesters behind. These approaches would not generally be commercially feasible, however, at least because in order to achieve the desired purity of the monoester, the solvent polarity would need to be adjusted to be quite high (large water content) so that the overall solubility of monoesters would be unreasonably low, resulting in excessive solvent requirements. A combined process, using a hydrocarbon and an alcohol/water extractant, would also be impractical on a large scale, because the hydrocarbon competes too strongly for the monoglyceride, resulting in low extraction factors and because recovering both the hydrocarbon and the alcohol/water adds cost.

The proposed preferred processes of the present invention, using an aqueous alcoholic extractant and using triglyceride fat/oil as a second phase to remove the diester, are unique and advantageous, but several obstacles needed to be overcome to obtain a useful process. For example, use of liquid-liquid extraction was perceived as counter-intuitive because the very nature of the desired product, monoesters, is that of an emulsifying agent. Such a product is used to stabilize emulsions of water in oil, such as triglycerides. The forming of a stable emulsion would prevent the operation of a liquid-liquid extraction system. The present process has worked satisfactorily in spite of this, although it is believed that low shear mixing will be useful and desirable in commercial scale practice, to prevent or inhibit formation of undesirable emulsions.

Secondly, triglyceride is one of the contaminating products in the crude monoglyceride stream, so intentionally adding triglyceride in order to help purify the monoglyceride is counter-intuitive. However, adding triglyceride has proven to be very useful in reducing the level of diester present in the final product.

Thirdly, residual triglyceride in the product is not readily removed (compared to a low boiling hydrocarbon such as hexane). However, it is believed that an important factor in defining purity of the monoester product may be how low the diester content is, or the ratio of monoester to diester content, rather than the absolute level of monoester content, or even the level of triester if it is below a threshold amount. After all, the purified monoester is frequently added to products along with triglycerides in the emulsified shortening. Thus, the purified monoester, in use, may well be mixed with triester, and it is generally removal of diester which is of greatest concern.

Indeed, in some applications, a product with a weight ratio of 90/5/5 monoglyceride, diglyceride, triglyceride may well be superior in functionality to one of 90/10/0. The greater difference in functionality between the monoester (monoglyceride) and the triester (triglyceride) is believed to cause triglyceride to be less interfering in the ability of monoester to form mesophases, than would be the same weight of diester.

It is also noted that the amount of triglyceride required, to facilitate the separation and purification, has been found to be relatively small. If, as an alternative to the triglyceride, a hydrocarbon, such as hexane, were to be used to facilitate the separation, a typical concentration might be 5–10 wt.-% of di- and triglyceride in the hexane. At this level, one might expect cosolvent effects, if any, to be relatively small and the system would behave as a hexane solution. Note that this corresponds to a system 0.7–1.5 mole % diglyceride in hexane, giving more than 65 molecules of hexane for every molecule of diglyceride. If triglycerides were needed at the same molar level as the hexane, the required amount of triglyceride would be at least 90 times, by weight, of the diglyceride stream or a concentration of less than 1.1 wt % diglyceride in the triglyceride stream. However, in preferred embodiments of the invention, where the triglyceride stream is subsequently used to generate more monoglycerides, the maximum level of triglycerides used typically is only about 1.5–3 times by weight of the diglycerides, and in other preferred embodiments it is expected to be no more than 8 times by weight of the diglycerides. The preferred minimum level of added triglycerides is expected to be greater than about 1 time by weight the diglycerides. At these levels of concentration, significant cosolvent effects are expected, and the system would not be characterized as a triglyceride stream, but rather as a mixture of di- and triglyceride.

It also might be expected that the diglyceride would act as a strong solvent to the monoglyceride, resulting in the ineffective extraction of the monoglyceride by the alcohol/water stream and leading to poor yields. This, however, has not been found. Based on batch results, it is anticipated that the extraction yield (extraction of monoglycerides into the alcohol/water extractant) in a countercurrent extraction train will exceed 90 wt % of the monoglycerides present in the feed.

Typically and preferably the extraction process is conducted at about 60° C.–80° C., and not above 120° C. Also typically and preferably it is conducted at about atmospheric pressure, and not above 5 atm. Also, typically and preferably the alcohol layer comprises 60–90% alcohol and 10–40% water, by weight. Most preferably it comprises about 70–85% alcohol, and 15–30% water, by weight. It is foreseen that typical preferred alcohol/water layers into which the monoglycerides are extracted will comprise about 75% alcohol/25% water, especially when the alcohol is ethanol. The typical and preferred alcohol will be ethanol because of high selectivity, high loading, low cost and acceptable toxic character.

Preferably the triglyceride added to the crude mixture comprises the same triglyceride as is present in the crude mixture prior to triglyceride addition. That is, in typical instances the crude monoglyceride mixture that is to be purified will have been made from a triglyceride mixture; and, the same type of triglyceride mixture which was used to make the crude monoglyceride mixture is the one added to the resulting crude monoglyceride mixture, prior to the extraction of the monoglyceride values into the alcohol/water feed, to facilitate the extraction. For example, if the process is used to purify a crude monoglyceride composition isolated from soybeans, then preferably the triglycerides added to the crude monoglyceride mixture to facilitate the extraction will be a crude mixture from soybeans, i.e. soybean oil, preferably with the same degree of hydrogenation. Advantages as a result of this will be apparent from the following more detailed descriptions.

B. A Process Flow Diagram

In FIG. 1, a preferred process flow for isolation and purification of monoesters such as monoglycerides according to the present invention is provided. The flow diagram of FIG. 1 is intended to be representative of more generally preferred applications according to the present invention. It is foreseen, however, that principles according the to present invention may be applied in variations from the process schematic shown in FIG. 1.

Referring to FIG. 1, the process generally includes three stages; i.e. Stage I (reference 5); Stage II, (reference 6); and, Stage III (reference 7). In Stage I, crude monoglyceride (monoester) mixtures are prepared. In Stage II, separation of a purified monoglyceride (monoester) mixture from a raffinate or residue mixture, is conducted. In Stage III, purified monoglycerides (monoesters) are isolated from the purified monoglyceride mixture. It is foreseen that Stages I, II and III can be conducted at one facility or more than one facility; and, they can be conducted in a batchwise or continuous process. However, it is noted that in one particularly preferred conduct of a process according to the present invention, cycling of certain feeds can be utilized to advantage. In such systems, generally the entire process will be conducted at a single facility. It may also be preferred in some applications to develop and use equipment that can be operated in a continuous flow-through process format, rather than a batch format, for efficiency.

1. Stage I—Generation of Crude Monoglyceride Mixture

As indicated above, the first stage of the process of FIG. 1, is indicated generally at reference 5, and comprises a stage whereat the crude monoglyceride mixture is generated. In general, the mixture is prepared in reactor 10. It is generated from a feed of glycerol 11 and a feed of triglyceride 12. In the reactor 10, the glycerol feed 11 and triglyceride feed 12 are mixed, and a mixture including monoglyceride(s) and other materials, typically diglyceride(s) and triglyceride(s), is generated. The reactor 10 is generally operated at about 220°–260° C., and under atmospheric pressure, although a variety of conditions may be utilized. The reactor 10 may be operated in a batch manner, or as a continuous process. Typical conventional operations for crude monoglyceride production can be utilized, and would involve a batch operation, with some base added as a catalyst. The typical base utilized will be sodium hydroxide or sodium glycollate.

The glycerol feed 11 may comprise either: an added glycerol stream from outside sources; a glycerol recycle stream from the reactor 10, as described, or both. Typically glycerol feed 11 will include both: added glycerol, indicated at 15; and, a glycerol recycle stream 16, as described. Streams 15 and 16 can be combined, at 17, using various metering techniques to obtain a preferred composition of glycerol feed in stream 11, to the reactor 10.

The triglyceride feed stream 12 may comprise an outside source (for example, natural product source) of triglyceride, cycled raffinate from an extraction step in Stage II, or both. Diglycerides will be present in the cycled raffinate and are a preferred feed component in the triglyceride feed stream. Typically and preferably feed 12 will include both. It is noted that naturally occurring triglycerides, such as palm oil or sunflower seed oil, are typically mixtures of triglycerides. More specifically, they comprise a mixture of fats or oils including the triglycerides of numerous fatty acids.

Still referring to Stage I (reference 5), reference 25 generally indicates the exit stream from reactor 10. Generally the exit stream 25, which comprises glycerol and a glyceride mixture, is directed into separator 26.

Either in separator 26, or immediately upstream, the reactor offstream 25 is preferably cooled, for example to about 60°–120° C., and typically the base catalyst is neutralized with an acid, usually phosphoric acid. Under these conditions, the glycerol will separate as a separate phase, since it is relatively insoluble in the glyceride mixture. At 30, the glycerol phase is shown removed from separator 26. In the particular system depicted, the glycerol phase from line 26 is directed for recycling, i.e. into recycle stream 16. The crude monoglyceride-containing fraction is shown removed from the separator 26, through line 35. Thus, line 35, in combination with a remainder of Stage I, represents a source of crude monoglycerides. It is arranged for direction of crude monoglycerides into an inlet feed of a primary counter-current extractor, as described below.

In general, the crude monoglyceride (monoester) phase from separator 26 will include some residual glycerol (alcohol) therein. Preferably, before it is directed into Stage II, it is treated to reduce the residual glycerol (alcohol) presence to less than 1% by weight. This can be conducted by a stripping step to remove residual glycerol. Equipment for conducting this is shown at 36. In general, any effective stripping step/equipment may be used, although a thin film evaporator or wiped film evaporator operating under vacuum will typically be preferred.

At 37, an optional crude monoglyceride bleed is shown. It is foreseen that since there will be some commercial demand for the crude monoglyceride mixture, in some systems it will be preferred to have a bleed 37 so it can be drawn off (or partially drawn off), and not directed in Stage II, if desired.

At 40, the crude monoglyceride mixture to be purified is shown directed into Stage II (reference 6).

As explained above, a variety of methods can be used for generation of the crude monoesters (monoglycerides). For example, as an alternative to being prepared from the reaction of glycerol with triglycerides, a crude mixture of mono- and diglycerides can be prepared from the reaction of glycerol with either fatty acids or with esters of fatty acids, such as methyl- and ethyl-esters. The equilibrium reaction product will generally comprise a crude mixture primarily of monoglycerides and diglycerides, with smaller amounts of triglycerides. The follow-up liquid-liquid purification process will be suitable for these reaction products as well.

2. Stage II—Liquid-Liquid Extraction

In general, in Stage II, crude monoglyceride is treated, through a liquid-liquid extraction, for isolation of a purified monoglyceride stream. Referring to FIG. 1, Stage II is generally indicated at reference 6. At 40, the crude monoglyceride stream is shown directed into Stage II for processing. In general, for preferred processes according to the present invention, the crude monoglyceride stream 40 is generated from a Stage I process, as described.

Preferred processes according to the present invention are conducted in such a manner that after the crude monoester composition is directed into Stage II, from then until isolation of the purified monoester: the monoester of interest is not distilled; the monoester is not subjected to temperatures in excess of about 140° C.; and, processes conducted under pressures greater than about 5 atm are avoided. Also in some preferred applications, no materials other than water, alcohol, triglyceride mixtures and similar generally recognized as safe materials, are added or used from that point forward in the process. Preferably hydrocarbon solvents (propane, butane, hexanes, etc.) are avoided to advantage.

In Stage II, reference 50 generally indicates the primary extraction equipment. Typically and preferably the extraction will be conducted at 60°–80° C., to ensure that it is conducted at a temperature above the melting point of any triglyceride component without being undesirably high. In general, the feed of monoglyceride mixture into the primary extractor 50 is shown at feed line 51; and, at line 52, the raffinate, i.e. the mixture substantially depleted with respect to monoglyceride values, is shown removed from the extractor 50. Herein when it is said that the mixture is "substantially depleted" with respect to "monoglyceride values" (or monoester values) it is meant that the monoglyceride (monoester) presence in the mixture has been reduced by at least 20%, due to extraction into a different phase, and separation. Typically and preferably at least 90% by weight of the monoester is extracted into the extractant.

At 54, the feed line for the phase into which the monoglyceride is extracted (i.e. the extractant) is shown directed into extractor 50. At 55, extractant, containing extracted monoglyceride values, is shown leaving the primary extractor 50. The material in line 55, then, comprises the liquid phase having the extracted monoglyceride values therein, i.e. it is a purified monoglyceride according to the present invention. This material is directed to Stage III, in typical processes, for separation of the monoglycerides (monoesters) from the extractant.

Still referring to FIG. 1, Stage II (reference 6), the material in feed 51 to the primary extractor 50 generally and preferably comprises: crude monoglyceride from line 40; and, triglyceride feed from line 58. That is, prior to being directed into primary extractor 50, crude monoglyceride compositions are modified by the addition of triglycerides thereto, and line 58 represents the source of added triglycerides. This will facilitate separation in the primary extractor 50, since the diglyceride components of the crude monoglyceride mixture will even more preferentially remain in the triglyceride-containing raffinate, rather than partition into the monoglyceride-containing alcohol/water phase. In typical processes, the alcohol/water feed will comprise, by weight, about 1 times to 6 times the weight of the monoglyceride-containing stream fed into the extraction.

For the preferred system shown in FIG. 1, Stage II includes a secondary extractor 60 (or wash system). The secondary extractor 60 is used to advantage in the following manner. The offstream 55 from the primary extractor 50 is directed into the secondary extractor 60, as indicated at inlet 61. Within the extractor 60, relatively less polar impurities such as diglyceride component in the purified monoglyceride stream 55 are preferentially washed into the triglyceride feed or triglyceride phase, from the alcohol/water purified monoglyceride phase (i.e. back extracted or washed). This triglyceride phase is shown directed into the secondary extractor 60 at line 65. Thus, within secondary extractor 60, the monoglyceride-containing alcohol/water phase from primary extractor 50 is extracted (or back extracted) with a triglyceride-containing phase, generating a triglyceride phase exiting extractor 60 in line 58, and an even further purified monoglyceride containing alcohol/water phase exiting secondary extractor 60 at 66.

In the system of FIG. 1, the triglyceride exiting the secondary extractor 60 is fed into the primary extractor 50, and to a certain extent is even cycled into reactor 10. Referring again to Stage I, if still further triglyceride needs to be fed into the feed stream 12 to reactor 10, it can be added via line 67.

In the preferred arrangement shown, the crude monoglycerides are added to Stage II downstream from the secondary extractor 60 and upstream from the primary extractor 50.

Still referring to FIG. 1, Stage II (reference 6), the exit flow 52 from primary extractor 50 is shown directed into separator 70. Water is added to separator 70, at line 71. Thus, at separator 70 an aqueous phase and an organic phase will be generated. The organic phase is shown removed from separator 70 at line 71, for direction into the triglyceride feed 12 to reactor 10. The aqueous phase is shown leaving separator 70 at line 72, for addition into the phase used in primary extractor 50, via line 73. This separator (which may contain more than one stage) is used to reduce the alcohol content in stream 52. Additional reduction in alcohol and water in stream 71 may be achieved by vaporization under vacuum.

Still referring to FIG. 1, Stage II, as indicated above, the monoglyceride enriched alcohol/water phase is shown leaving the secondary extractor 60 at line 66, for direction into Stage III.

Herein the term "fluid direction conduit arrangement" is used generally to refer to the various fluid conduits in the system for directing fluid flow between the various reactors, separators and extraction equipment. For example, the fluid direction conduit arrangement includes a fluid conduit 58 from the triglyceride extractant outlet of the secondary counter-current extractor 60, to the crude monoester composition inlet feed 51 of the primary counter-current extractor 50; and, it also includes a fluid conduit 55 from the alcohol/water extractant outlet of the primary counter-current extractor 50, into the secondary counter-current extractor inlet 61. These portions of the fluid direction conduit arrangement are generally found in Stage II, FIG. 1. The term "fluid direction conduit arrangement" is intended to include within its scope any pipes, fittings, pumps, valves, or other equipment needed or desired for appropriate operation.

3. Stage III—Monoglyceride Isolation From The Alcohol/Water Mixture

At this point, the purified monoesters are present as a solution in aqueous alcohol. A number of options are available to recover the monoesters into a useful form. For example, the aqueous alcohol/purified monoester stream could be back extracted with a low boiling hydrocarbon, such as hexane, and the hexane could then be stripped from the monoglycerides. The recommended hexane volume for such an operation would typically be a mass flow rate at least equal to the aqueous alcohol flow rate, in order to recover a significant portion of the monoglycerides.

An alternative method for recovery would be to cool the aqueous alcohol/monoglyceride stream to precipitate or crystallize the monoglycerides. In general, the "best" temperature for the cooled stream would be a function of the degree of hydrogenation of the monoglycerides. Satisfactory results would typically be obtained at temperatures of about 10°–30° C.

A third method for product recovery would be to add water to the aqueous alcohol/monoglyceride stream, reducing the solubility of the monoglycerides. Adding sufficient water to make an aqueous alcohol of greater than 50 vol. % water, and preferably greater than 70 vol. % water has been observed to cause separation of a significant portion of the monoglycerides. In general, centrifugation has been found useful for separating the two phases after the water addition.

A still further method of product recovery is to flash or distill the alcohol (ethanol), preferentially to the water, from the solution in order to form a more water-rich aqueous alcohol solution, resulting in easier separation of a monoglyceride-rich phase.

A still further method to recover the product is to strip, preferably under vacuum, the water and alcohol (ethanol) to form a molten stream of substantially pure, dry, monoglycerides. A thin film, wiped film, or scraped film evaporator would typically be preferred choice for the final stripping, while a shell and tube evaporator might be useful to remove the bulk of the aqueous alcohol.

A still further method to recover product would be to spray dry under vacuum, preferably with a solid carrier such as flour or milk solids to aid in producing a granular product. Freeze drying can also be a useful technique to remove the final traces of aqueous alcohol from a concentrated stream.

Bearing these various possibilities in mind, general reference will be made to FIG. 1, and the isolation. From the above discussions, variations in equipment to accommodate different approaches to isolation will be apparent.

Reference 7, FIG. 1, generally represents Stage III, i.e. the stage whereat the monoglyceride enriched (or monoester enriched) alcohol/water liquid phase is treated for isolation of monoglyceride (monoester) values therefrom. In general, this phase is shown leaving the liquid-liquid extraction process, Stage II line 66, and is shown directed into Stage III, at 80. For the particular preferred system shown, in Stage III, feed 80 is directed into a distillation apparatus 81. The distillation apparatus 81 is operated to distill or vaporize the alcohol/water mixture, shown exiting at line 83, from the reactor bottoms containing purified monoglycerides, shown leaving the distillation apparatus 81 at line 85. The distillation apparatus 81 is preferably comprised of multiple stages. In the first stage, the bulk of alcohol/water mixture is preferably removed in an evaporator capable of handling a large volatile content, such as a rising film evaporator, falling film evaporator, shell and tube evaporator, or other equipment. The temperature should be maintained at 140° C. or less, preferably less than 100° C. at suitable pressure/vacuum for the alcohol/water mixture being used. Multiple effect evaporators might be used to achieve greater energy economy. In the later stages, the remainder of the alcohol/water mixture is removed to create a devolatilized molten product. A thin film evaporator or wiped film evaporator is believed to be suitable for this stage. This can be conducted with temperatures of about 140° C., and preferably no higher than 100° C., and at pressures of 200 mm Hg or less, preferably 50 mm Hg or less. Thus, within distillation apparatus 81, the monoglycerides are preferably not themselves distilled, but rather the ethanol/water solvent is distilled (or stripped) from the monoglyceride reactor bottoms. It is important to understand that in most preferred operations of systems according to the present invention, the isolated monoglycerides are not themselves ever actually distilled.

Still referring to Stage II, FIG. 1, the ethanol/water distilled away from the mixture, at line 83, is shown being cycled into the primary extractor 50, Stage II. The distillation bottoms 85, containing monoglycerides, are directed into separator 90. In separator 90, they can be washed with water or ethanol, for further purification, and recrystallization can be conducted, if desired. Purified monoglycerides from separator 90 are removed through line 91. If desired, alcohol/water or water utilized for separation or purification in separator 90 is shown directed via line 93, into line 94, whereat it is mixed with the distilled ethanol/water from line 83, and is cycled into the primary extractor 50 via line 54. In a preferred embodiment, the distillation bottoms 85 are of the desired purity and devolatilized to an extent that the separator 90 can be bypassed, and the distillation bottoms 85 can be further processed, as described below for the product via line 91.

The purified monoglycerides shown removed from separator 90 via line 91 can be sold as product, or further processed, for example by drying, flaking, pelletry, hydration or mixing with triglyceride fat/oil.

From the above discussion of FIG. 1, it is apparent that processes according to the present invention are particularly advantageous, since they are well developed for efficient operation to facilitate generation and isolation of monoglycerides. For example, the triglycerides added to facilitate the separation, in Stage II, are cycled into Stage I, to facilitate preparation of the monoglyceride mixture. Preferably, ethanol/water utilized as the liquid phase into which the partitioning of monoglyceride occurs during the liquid-liquid extractions, is cycled back into Stage II, following isolation of the monoglycerides therefrom, to advantage.

Utilization of primary and secondary extractors 50 and 60 respectively, in Stage II, is unique and highly advantageous. The extraction which occurs in secondary extractor 60 is of diglycerides into a triglyceride-enriched feed, and results in a fine tuning of the purified monoglyceride stream 55, for preferred partitioning of diglycerides that may be present into the triglyceride feed. Thus, any diglyceride presence, from extraction into the water/ethanol phase in extractor 50, is greatly reduced.

Line 51, directed in the primary extractor 50 includes triglyceride-enriched crude monoglyceride mixture. The term "triglyceride-enriched crude monoglyceride mixture" as used herein, in this context, is meant to refer to a crude monoglyceride mixture to which triglycerides have been added. Preferably the triglyceride-enriched crude monoglyceride mixture is a mixture to which there has not been an addition of other non-alcoholic solvents, beside the triglycerides, i.e. hydrocarbon solvents such as propane, butane, hexanes, etc. That is, preferably the monoglyceride mixture is modified by addition thereto of triglycerides, but not by addition of other solvents, to facilitate extraction.

The triglyceride(s) generates a preferred organic phase for partitioning and separation, in the primary extractor 50. In particular, it creates an environment in greater contrast to the alcohol/water environment of the extractant, so that the diglyceride component will more preferably remain in the organic phase, relative to partitioning into the alcohol/water phase. Diglyceride which does partition into the alcohol/water phase, however, can be greatly removed in the secondary extraction process. In general, then, in processes according to the present invention the composition of the phases in the primary extractor 50 and secondary extractor 60 will be balanced to achieve a preferred efficiency of separation.

IV. Preferred Conduct of the Extractions

In general, when processes according to the present invention are practiced with both a primary extraction and a follow up wash step (i.e. the secondary extraction), the process may be characterized as a liquid-liquid fractionation or fractional extraction. With such practices, the ultimate purity obtained for the monoesters approaches 100%, generally limited only by the solubility of the wash solvent (i.e. the triglycerides) in the extraction phase.

When processes according to the present invention are conducted without the secondary extraction, or wash step, the ultimate purity obtainable for the isolated monoesters is essentially limited by the ratio of monoesters and diesters in the crude, and the selectivity, α, of the solvent. Selectivity (for monoester versus diester) is generally given by the formula:

$$\alpha = K_{mono}/K_{di}$$

wherein the K's are partition coefficients (extraction coefficients) defined as K=y/x, where y is the mass fraction of the relevant material in the extract, and x is the mass fraction of the relevant material in the raffinate phase. Of course similar formulae can be written for selectivity of monoesters versus triester, or diester versus triester.

For extractions involving a large number of stages, the monoester purity (excluding triglyceride) is given by the formula:

$$\% ME = 100 \times \left[ \frac{r \times \alpha}{1 + (r \times \alpha)} \right]$$

wherein r=ME/DE (mass ratio) in the crude (ME being monoester, DE being diester). Under some typical conditions, involving monoglyceride isolation, a composition of the crude would typically be about 60 wt % monoglyceride, 35 wt % diglyceride, and 5 wt % triglyceride, giving an r equal to 1.71. The required value of a to achieve a desired monoglyceride purity can then be calculated, with a $\alpha=5.3$ for 90% MG and $\alpha=11.1$ for 95% MG purity. Requiring a greater than or equal to 11.1 limits the aqueous alcohol compositions and levels of monoglycerides which may be used. This is in sharp contrast to the system with a wash section, or secondary extraction, where there are no similar restrictions on $\alpha$, since the secondary extraction or wash removes or reduces undesired diglycerides from the extractant.

Thus, in general, a preferred level of purification of monoglycerides in preferred systems according to FIG. 1 is generally obtained through control of:

1. The conditions to the primary extraction;
2. The conditions of the secondary extraction; and
3. The relative conditions of the primary extraction and second extraction.

In general, fatty acid esters such as monoglycerides and diglycerides are insoluble in water but are very soluble in low molecular weight alcohols, i.e., $C_1$–$C_3$ alcohols such as ethanol. However, although diglycerides are somewhat soluble in ethanol, they are less so than monoglycerides. The liquid phase into which the monoglyceride is extracted in the primary extractor 50, then, is preferably a phase comprising a mixture of alcohol and water. The mixture should be tuned to obtain a preferred amount of monoglyceride partitioning therein, with control on a preferred maximum amount of diglyceride partitioning which also occurs in that stream. The amount of diglyceride extraction into that stream, which can be accepted, turns in part upon the level of diglyceride removal which can be readily conducted in the secondary extraction. The more water which is added to the ethanol, the more specific will be the partitioning between diglyceride and monoglyceride in the primary extraction. That is, with an increase in water, the liquid phase into which the monoglyceride is being extracted has a lower propensity to also pick up (extract) diglycerides, i.e. the extraction is more selective. Of course it also has a lower propensity to pick up monoglycerides.

In general, it is desired to utilize conditions in which relatively high load of monoester can be obtained. By this it is meant a load of at least about 10 g (preferably at least 15 g) per 100 g extractant. Thus, it is undesirable to add so much water that that solubility of the monoester, under the extraction conditions, is below these preferred amounts. This will involve some sacrifice in purity, at least at the primary extraction stage. However, the secondary extraction or washing in preferred applications, addresses this.

Similarly, the amount of triglycerides added to the crude monoglycerides to facilitate a separation, will depend upon the level of partitioning with respect to the diglycerides preferred. The more triglycerides added, the lower will be the propensity of the diglycerides to partition into the alcohol and the greater will be the propensity of the diglycerides to remain in the organic (triglyceride/diglyceride) phase during the primary extraction. Thus, the level of triglycerides added can be balanced with the ethanol/water mix, to obtain a preferred partitioning of diglycerides.

A variety of extraction techniques, and extraction equipment, can be utilized for both the primary extractor 50 and secondary extractor 60. In general, counter-current extractors will be preferred, typically configured for at least two stages and more preferably at least three stages in each extraction. The choice of the number of stages is based on the desired extend of recovery, purity and overall economics. For a given recovery and purity, a system with more stages will allow higher loading of the extractant phase, reducing product recovery costs. In a typical and preferred system, the loading will be at least 10% by weight, monoester in the extractant. In more preferred systems, the loading will be at least 15% by weight, monoester in the extractant.

Typically, the amount of triglyceride fed into the system will be balanced with the amount of purified monoglyceride (crude monoglycerides) removed so that the system operates at steady states with neither accumulation nor depletion. While maintaining the constraints of material balance, triglyceride can be fed into the system through either line 67 or line 65. In preferred embodiments, the triglyceride is fed primarily through line 65. This maximizes the triglyceride flow through the extractor, diluting the diglyceride, while allowing high purity monoglyceride production with a smaller extractant flow rate. This results in higher loading and reduced product recovery costs. If the flow rate through line 37 is more than about 4 times the flow rate through line 91 additional triglyceride may be needed, and it can be fed through line 67, to obtain higher extractant loading.

V. Propylene Glycol Monoesters (PGME) and Other Monoesters

Processes as shown in FIG. 1, generally described above, can also be utilized to isolate other monoesters, for example propylene glycol monoesters, using analogous techniques. In general, the feed in line 11 would include propylene glycol, from line 15. Thus, the recycle at 30 in 16 would be propylene glycol, and the crude mixture at line 35 would comprise a mixture of propylene glycol monoester with diester and mono-, di-, and triglycerides.

In general, the preparation of propylene glycol fatty acid esters is possible from a number of routes. For example, propylene glycol and triglycerides can be reacted together to give a reaction product comprising primarily monoesters of propylene glycol, with lesser amounts of propylene glycol diesters, monoglycerides, diglycerides, and triglycerides, after removal of the excess propylene glycol and glycerol. A second route is through the reaction of propylene glycol with fatty acid or fatty acid esters, such as methyl or ethyl esters of fatty acids. The product from this reaction will generally be a mixture comprising primarily mono and di-esters of propylene glycol. A third route is to react propylene oxide with fatty acid, leading to a mixture of monoester isomers.

The proposed liquid-liquid purification process described herein will be useful for materials prepared at least according to the first or second routes. It is presently believed that the products from the first reaction scheme would be readily separated in a stream comprising primarily propylene glycol monoester and monoglyceride, and, if desired, the process could be tuned to provide a stream comprising primarily propylene glycol monoester. The reaction product from the second scheme is believed to be readily separable into a substantially pure propylene glycol monoester stream.

As to the third approach, the monoesters are generated in a substantially pure form.

The following may be useful, for considering a system for purifying PGME. Typical crude PGME product, made from reacting propylene glycol with triglycerides, would include, by weight, about 60–65% PGME; about 5–10% propylene glycol diester; about 10–15% monoglyceride; about 5–9% diglyceride; and about 5–8% triglyceride. The purification approach described herein would generally lead to an isolation of much of the PGME and MG values, from the remainder. It would particularly concern reductions in the diester and diglyceride amounts. The triglyceride amount may still be relatively significant, in the final isolated material. However, the material will still be preferred, due to the reduction in the presence of diglycerides.

VI. Some Advantageous Operations; Products

Processes according to the present invention can be utilized in preferred manners, to obtain a great many advantages. For example, they can be applied to obtain a mixture containing at least 90% by weight of monoester, relative to diester and triester, without the need for distilling the esters. This can result in a cost advantage, and in some instances preferred product characteristics.

Sometimes processes which involve distillation of monoesters such as monoglycerides or propylene glycol monoesters, are associated with the generation of "off tastes" and/or "off aromas" in the final product. The specific source of these off flavors or off aromas is not presently known. However, it seems to be associated with the conduct of distillation processes, i.e. processes that concern heating mixtures containing the monoglyceride (or propylene glycol monoester) of interest until they vaporize under the distillation conditions, typically 240° C. Methods according to the present invention can be conducted in overall process systems wherein no distillation of the monoglyceride product (or PGME product) occurs anywhere in the system, and in which, after Stage II is begun, the monoester to be purified is never subjected to temperatures above about 140° C., and typically not above 100° C. This can lead to the generation of product not possessing the same extent of "off flavor" or "off odor" characteristic sometimes associated conventional processing. In addition by avoiding exposure to high temperature, the product may be more shelf stable. The processes of the most preferred systems such as shown in FIG. 1 are systems in which no distillation of the monoglyceride (or PGME) occurs.

In addition, processes according to present invention can be utilized or "tuned" to obtain preferred levels of purity for the monoglycerides. In general, with distillation processes, the upper limit of purification obtained in the commercial practice in the past has been about 3% diglyceride residual. With extraction processes according to the present invention, purifications on the order of less than 5% diglyceride residual, typically less than 3% and often even less than 2% diglyceride residual can be readily obtained, if desired.

Purified monoglycerides according to the present invention can be utilized to prepare preferred compositions, such as oil compositions including the emulsifier added thereto, for use in various food industries or as dough preparations. These will in general be advantageous, since they will include: a preferred ratio of monoglyceride (or PGME) to diglyceride (or diester); and, the avoidance of the provision of the off flavor or off odor component, generally associated with a monoglyceride material that has been distilled.

In addition to use as an emulsifier in food systems, purified monoglycerides according to the present invention can be used as a starting material for the production of a number of related emulsifiers. For example, acetylated monoglycerides, citric acid esters of monoglycerides, sodium salts of citric acid esters of monoglycerides, diacetyl tartaric acid esters of monoglycerides, and lactic acid esters of monoglycerides are all emulsifiers derived from monoglycerides. It is anticipated that preferred such materials can be prepared from purified monoglycerides according to the present invention. Such materials would have a variety of uses in the food industry, either used alone or in combination to provide emulsion stabilization, to provide improved aeration and foam stabilization, to form complexes with starch and prevent staling and sticking, to strengthen dough to retain its rise, and to prevent changes in crystal structure during storage. Useful levels generally range from 0.5 wt % up to 8 wt %, depending on the product and application. The purified monoesters provided by the present invention are believed to be suitable replacements for distilled monoesters at about the same use levels. In addition, the monoesters of the present invention may be a cost effective replacement, in some instance, for crude monoesters and the use level would be based on comparable amount of monoester.

The monoesters of the present invention would be provided in a similar form to the existing products, as a liquid or solid, bulk, powder, flake, 50 lb cube, dry or hydrated, with or without the appropriate antioxidants, crystal habit modifiers, and carriers.

Processes according to the present invention can be operated in generally preferred, economic, manners, due to the recycling capabilities discussed above with respect to FIG. 1. Also pressurized conditions, and thus for many steps equipment associated with pressurized conditions, can be avoided. Finally, heating material to in excess of 140° C. is generally avoided, leading to an energy savings, and reduced formation of oxidation products and/or off-flavors.

Processes according to the present invention are well developed for utilization in the preparation for a variety of monoglycerides or monoglyceride mixtures. The processes are not sensitive to whether or not the triglyceride materials fed into the system are pure, and whether they are liquid, solid or a mixture thereof. The separations will be effective under any of these conditions, and thus the techniques are widely applicable.

In general, the processes described herein can be performed using triglycerides of fatty acids or fatty acid esters of any desired degree of saturation, depending on the desired functionality of the final product. Typically, products can be made with any desired degree of hydrogenation, specified by the iodine value (IV), ranging from IV=2 or less, to IV=90 or higher, if desired. Products with a low IV (i.e., less than 5) are frequently used as emulsifying agents in margarine, cake shortening and coatings for candies. They are also used in baked products or in potato products. In these latter applications, the ability to form a complex with amylose starch is useful to provide antistaling, crumb conditioning agent, and in whipped toppings where the foam stabilization properties are useful. Low IV monoglycerides are also frequently used as starting points in the production of other emulsifier products, such as acetylated monoglycerides, citric acid esters of monoglycerides, sodium salts of citric acid esters of monoglycerides, diacetyl tartaric acid esters of monoglycerides, and lactic acid esters of monoglycerides.

The high IV (greater than 40) products are typically used when a softer or more liquid product is required. For example, an IV 40 monoglyceride might be useful for icing or soft margarine, and IV 70 or IV 90 monoglycerides might be used when even softer consistency is desired.

In general, processes according to the present invention are designed to be operated, if desired, above the melting point of the materials in question, thus treating the product essentially in a liquid state. In general it is believed that this will give a process which is readily adapted for a variety of oils of differing degrees of saturation. The separation is driven primarily by functionality, especially the balance between polar and nonpolar moieties. Because of this, the processes are believed to be applicable to either mixtures of oils of different IVs or to oils of intermediate IV, which may inherently include a variety of compounds, operating with or without causing an undesired fractionation of the material on the basis of its degree of saturation. Processes which rely on melting point differences, such as fractional crystallization, are not believed to be as robust in this sense. Instead, the separation will depend strongly on the IV of the material, because saturation strongly influences melting point.

With respect to iodine value (IV), it is noted that this measure of unsaturation can be measured using standard techniques, such as AOCS method #CD1B87, "The iodine value of fats and oils using the cyclohexane method", incorporated herein by reference.

VII. Preferred Equipment

From the following examples of certain preferred equipment, general principles of the present invention and its application will be even further understood.

For example, for the primary and secondary extractors equipment such as: mixer/settler tanks; pulsed columns; baffle columns; reciprocating plate columns; Podbrelnick centrifugal contactors; rotating disc contactor columns; and similar devices may be used. Such equipment provides the required cycles of intimate contacting between phases, with follow-up phase separation.

For the various separators, a low shear mixing system is preferred to reduce the likelihood of emulsion formation.

VIII. Experimental

EXAMPLE 1

Comparison of Extraction Using Aqueous Isopropanol with either Triglyceride Oil or Hexane as a Carrier Phase Single stage, equilibrium experiments were performed by mixing together aqueous isopropanol (containing either 15 or 25% water by volume), a less polar carrier phase of either IV 78 corn oil or hexane, and crude monoglycerides. The samples were made up into test tubes, heated in a temperature controlled water bath, and mixed. After mixing, the samples were allowed to stand in the water bath for at least 1 hour before sampling. Aliquots were taken of each phase, for the systems which formed two phases, and the aliquots were analyzed by gas chromatography after being evaporated at 110° C. in flowing nitrogen. The monoglyceride content for the samples in the table below were 2 grams crude monoglyceride per 10 ml of combined solvent. Samples were also made at 4 grams crude monoglyceride per 10 ml of combined solvent, but these did not generally result in more than a single phase. The solvents were added at a volume ratio of polar solvent to less polar solvent of either 1/1 or 2/1. The initial composition of the crude monoglycerides was approximately 60%/35%/5% by weight of monoglyceride/diglyceride/triglyceride. The selectivity for the monoglyceride over diglycerides and selectivity for monoglycerides over triglycerides are also reported.

TABLE I

Test results over digylcerides oil as less polar phase.

| Temp (C.) | Water vol % | [1]Polar /Non-polar | [2]MG, wt % polar | [3]DG, wt % polar | [4]TG, wt % polar | [5]MG, wt % non-polar | [6]DG, wt % non-polar | [7]TG, wt % non-polar | [8]Selectivity MG/DG | [9]Selectivity MG/TG |
|---|---|---|---|---|---|---|---|---|---|---|
| 45 | 15 | 1 | 42   | 24   | 34   | 11   | 17   | 72   | 2.7  | 8.1  |
| 45 | 15 | 2 | 43.6 | 15.6 | 40.8 | 12.6 | 11.4 | 76   | 2.5  | 6.4  |
| 60 | 15 | 1 | 48.8 | 13.9 | 37.3 | 8.6  | 10.1 | 81.2 | 4.1  | 12.4 |
| 60 | 15 | 2 | 31   | 13.7 | 55.3 | 13.1 | 12.1 | 74.8 | 2.1  | 3.2  |
| 45 | 25 | 1 | 64   | 21   | 15   | 8    | 16   | 76   | 6.1  | 40.5 |
| 45 | 25 | 2 | 64.3 | 13.3 | 22.4 | 9.7  | 10.4 | 79.9 | 5.2  | 23.6 |
| 60 | 25 | 1 | 75.1 | 11.4 | 13.5 | 9    | 14.1 | 76.8 | 10.3 | 47.5 |
| 60 | 25 | 2 | 66.8 | 16.9 | 16.2 | 10   | 14.3 | 75.7 | 5.7  | 31.2 |

[1]Polar/non-polar is volume ratio of polar solvent to less polar solvent; i.e. water and isopropanol mix/added triglycerides.
[2]Monoglyceride wt % (based on total weight glycerides) in polar phase.
[3]Diglyceride wt % (based on total weight glycerides) in polar phase.
[4]Triglyceride wt % (based on total weight glycerides) in polar phase.
[5]Monoglyceride wt % (based on total weight glycerides) in non-polar phase.
[6]Diglyceride wt % (based on total weight glycerides) in non-polar phase.
[7]Triglyceride wt % (based on total weight glycerides) in non-polar phase.
[8]Selectivity in this column is calculated from (MG wt % in polar phase ÷ DG wt % in polar phase) ÷ (MG wt % in non polar phase ÷ DG wt % in non polar phase).
[9]Selectivity in this column is calculated from (MG wt % in polar ÷ TG wt % in polar phase) ÷ (MG wt % in non polar phase ÷ TG wt % in non polar phase).

Test results using hexane, under the same conditions, resulted in single phase systems or in two phase systems with selectivity near 1, yielding no purification of the crude monoglycerides.

This example shows the usefulness of the system of aqueous isopropanol/triglyceride for obtaining purification of monoglycerides. The selectivity of monoglyceride to diglyceride is sufficient, but the selectivity of monoglyceride to triglyceride is lower than desired. The selectivity is higher at higher water concentration, and the preferred water content for use with isopropanol is 25 vol % or greater.

Hexane was shown to be unsuitable for use as a second phase. Other hydrocarbons are expected to behave similarly.

EXAMPLE 2

Comparison of Extraction using Aqueous Ethanol with Either Triglyceride Oil or Hexane as Carrier Phase Single stage, equilibrium experiments were performed by mixing together aqueous ethanol (containing either 25 or 35% water by volume), a less polar carrier phase of either IV 78 corn oil or hexane, and crude monoglycerides. The samples were made up into test tubes, heated in a temperature controlled water bath, and mixed. After mixing, the samples were allowed to stand at least 1 hour before sampling. Aliquots were taken of each phase, for the systems which formed two phases, and the aliquots were analyzed by gas chromatography after being evaporated at 110° C. in flowing nitrogen. The monoglyceride content for the samples in the table below were 2 or 4 grams crude monoglyceride per 10 ml of combined solvent. The solvents were added at a volume ratio of polar solvent to less polar solvent of either 1/1 or 2/1. The initial composition of the crude monoglycerides was approximately 60%/35%/5 by weight of monoglyceride/diglyceride/triglyceride. The IV of the crude monoglycerides was approximately 70. The selectivity of the polar phase for monoglyceride over diglycerides, selectivity for monoglyceride or triglyceride, and the partition coefficient for the monoglycerides are also shown. In Tables II and III, the reports for the experiments are shown and analogous headings to those used in Table I have analogous meanings.

This example shows a system of aqueous ethanol/triglycerides possesses the beneficial features of high monoglyceride to diglyceride selectivity, high monoglyceride to triglyceride selectivity, and a high extraction coefficient (corresponding to high loading of the extractant phase). The aqueous ethanol/hexane system has good selectivity, but very low extraction coefficients (low loading of the extractant phase).

TABLE II

Test Results using Triglyceride Oil as Less Polar Phase

| Temp °(C.) | Water vol % | Polar/ less polar | MG, wt % polar | DG, wt % polar | TG, wt % polar | MG, wt % less polar | DG, wt % less polar | TG, wt % less polar | Fat g/ml in polar phase | Fat g/ml in less polar phase | [1]Selectivity MG/DG | [4]Selectivity | [3]Partition coefficient K (mono) |
|---|---|---|---|---|---|---|---|---|---|---|---|---|---|
| 2 g/ 10 ml | | | | | | | | | | | | | |
| 45 | 25 | 1 | 83.1 | 9.1 | 7.8 | 9 | 11.6 | 79.4 | | | 11.8 | 94 | |
| 45 | 25 | 2 | 82.7 | 13.7 | 3.7 | 10.1 | 15.4 | 74.5 | 0.07 | 0.44 | 9.2 | 165 | 1.35 |
| 60 | 25 | 1 | 86.8 | 8.4 | 4.8 | 9.5 | 12.2 | 78.4 | | | 13.3 | 149 | |
| 45 | 35 | 1 | 81.6 | 9.3 | 9.1 | 12.1 | 11.8 | 76.1 | 0.1 | 0.64 | 8.6 | 56 | 1.03 |
| 60 | 35 | 2 | 89 | 7.4 | 3.6 | 11.8 | 14.9 | 73.3 | 0.12 | 0.91 | 15.2 | 164 | 0.99 |
| 4 g/ 10 ml | | | | | | | | | | | | | |
| 45 | 25 | 1 | 66.1 | 16 | 18 | 20.5 | 16.9 | 62.6 | 0.22 | 0.59 | 3.4 | 11 | 1.2 |
| 45 | 35 | 2 | 81.1 | 13.1 | 5.8 | 32.8 | 21.1 | 46 | 0.05 | 0.58 | 4 | 20 | 0.21 |
| 60 | 35 | 1 | 82.3 | 10.4 | 7.3 | 38.2 | 26.5 | 35.3 | 0.07 | 0.74 | 5.5 | 11 | 0.21 |

[1]In this column, selectivity is for MG over DG.
[2]In this column, selectivity is for MG or TG.
[3]In this column, the partition coefficient K is wt. fraction MG polar/wt. fraction MG in less polar phase.

TABLE III

Results Using Hexane As Less Polar Phase

| Temp (C.) | Water, vol % | Polar/ Less polar | MG, wt % polar | DG, wt % polar | TG, wt % polar | MG, wt % less polar | DG, wt % less polar | TG, wt % less polar | Fat, g/ml polar | Fat, g/ml less polar | Selectivity MG/DG | Partition coefficient, K (mono) |
|---|---|---|---|---|---|---|---|---|---|---|---|---|
| 2/10 mg | | | | | | | | | | | | |
| 45 | 25 | 1 | 95.3 | 4.7 | 0 | 59.3 | 36.3 | 4.3 | — | — | 12.4 | — |
| 60 | 25 | 1 | 92.7 | 7.3 | 0 | 58.8 | 35.5 | 5.7 | — | — | 7.7 | — |
| 60 | 25 | 2 | 78.6 | 20.4 | 1 | 58 | 36.4 | 5.6 | 0.07 | 0.64 | 2.4 | 0.14 |
| 45 | 35 | 2 | 93.6 | 6.4 | 0 | 58.5 | 35.8 | 5.7 | 0.01 | 0.19 | 9 | 0.04 |
| 60 | 35 | 1 | no data | no data | no data | 59.5 | 35.2 | 5.3 | 0.01 | 0.43 | — | <0.03 |
| 4/10 mg | | | | | | | | | | | | |
| 45 | 25 | 2 | 83.2 | 16.8 | 0 | 58.4 | 35.6 | 6.1 | 0.02 | 0.22 | 3 | 0.1 |
| 60 | 25 | 1 | nd | nd | nd | 59.4 | 35.3 | 5.3 | 0.01 | 0.47 | — | <0.05 |
| 45 | 35 | 1 | 87.8 | 12.2 | 0 | 60.2 | 35 | 4.7 | 0.01 | 0.26 | 4.2 | 0.03 |
| 60 | 35 | 2 | 84.1 | 15.9 | 0 | 58.4 | 36.2 | 5.4 | 0.04 | 0.68 | 3.3 | 0.09 |

EXAMPLE 3

Extraction Using Aqueous Methanol and Triglyceride

Single stage, equilibrium experiments were performed by mixing together aqueous methanol (containing either 5 or 10% water by volume), a less polar carrier phase of IV 40 soybean oil, and crude monoglycerides. The samples were made up into test tubes, heated in a temperature-controlled water bath, and mixed. After mixing, the samples were allowed to stand at least one hour before sampling. Aliquots were taken of each phase, for the systems which formed two phases, and the aliquots were analyzed by gas chromatography after being evaporated at 110° C. in flowing nitrogen. The monoglyceride charge for the samples in the table below were 1 or 2 grams crude monoglyceride per 10 ml of combined solvent. The solvents were added at a volume ratio of polar solvent to less polar solvent of 2/1. The initial composition of the crude monoglycerides was approximately 60%/35%/5% by weight of monoglyceride/diglyceride/triglyceride. The IV of the crude monoglycerides was approximately 70. The selectivity of the polar phase for monoglyceride over diglycerides, the partition coefficient for the monoglycerides, and the selectivity for monoglycerides over triglycerides are also shown. The results are reported in Table IV. In Table IV analagous headings to those used in Table I have analogous meanings.

The example shows the high selectivity (monoglyceride over diglyceride and monoglyceride over triglyceride) and high extraction coefficient (high loading of the extractant phase) for the aqueous methanol/triglyceride system. It appears to be a very feasible system.

%, or 30 vol % water in ethanol). IV 40 soybean oil was added and the samples were heated to 60° C., mixed, and allowed to equilibrate for at least one hour. The charge of crude monoglyceride was either 10, 15, or 20 g/100 ml combined solvent phases, and the ratio of the solvent phases was either 2/1, 3/1, or 4/1 polar/less polar. Aliquots were taken and analyzed for fat content (residue upon evaporation) and for fat composition by GC. The results and calculated values of selectivity (monoglyceride to diglyceride content in polar phase over less polar phase) and extraction coefficient (concentration of monoglycerides in polar phase divided by concentration of monoglycerides in less polar phase) are shown in Table A below. A summary table is also given, showing the mean values for selectivity and extraction coefficient as a function of loading and water content in the aqueous ethanol.

Summary Table

| Charge g/100 ml | Water vol % | Selectivity | K (mono) |
|---|---|---|---|
| 10 | 16 | 15 | 2.4 |
| 10 | 23 | 14 | 1.5 |
| 10 | 30 | 23 | 1.0 |
| 15 | 16 | 9 | 1.8 |
| 15 | 23 | 16 | 1.3 |
| 15 | 30 | 12 | 0.8 |
| 20 | 16 | 7 | 2.4 |
| 20 | 23 | 9 | 1.5 |
| 20 | 30 | 10 | 1.4 |
| 20 | 60* | 7 | 0.7 |

TABLE IV

Results Using Aqueous Methanol and Triglyceride

| Temp (C.) | Water vol % | Choose (crude mono per 10 ml solvent) | MG, wt % polar | DG, wt % polar | TG, wt % polar | MG, wt % less polar | DG, wt % less polar | TG, wt % less polar | Fat, g/ml polar | Fat, g/ml less polar | Selectivity MG/DG | Partition coefficient K (mono) | Selectivity MG/TG |
|---|---|---|---|---|---|---|---|---|---|---|---|---|---|
| 60 | 5 | 10 | 89.7 | 10.3 | 0 | 6.3 | 9.3 | 84.4 | 0.08 | 0.67 | 12.9 | 1.68 | — |
| 60 | 5 | 20 | 83.4 | 13.3 | 3.3 | 8.7 | 13.4 | 77.9 | 0.14 | 0.78 | 9.7 | 1.68 | 226 |
| 60 | 10 | 10 | 95 | 5 | 0 | 4.7 | 7.1 | 88.2 | 0.06 | 0.74 | 28.7 | 1.51 | — |
| 60 | 10 | 10 | 82.3 | 7.5 | 10.2 | 14 | 14.9 | 71.1 | 0.11 | 0.82 | 11.7 | 0.8 | 41 |

EXAMPLE 4

Evaluation as Possible Use of Aqueous Butanol with Hexane

Crude monoglycerides (2 gm, IV 70) was weighed into test tubes and 5 ml of a mixture of 88 vol % butanol and 13 vol % water was added. The samples were gently heated to dissolve the crude monoglycerides. 5 ml of hexane was added to the solution and the phases were mixed by gentle shaking. The tubes were placed into a temperature controlled bath (45° C. or 60° C.) for at least one hour. The aqueous butanol/hexane/crude monoglyceride system was observed to form a single phase solution and is not suitable for use in liq-liq extraction processing to purify monoglyceride.

EXAMPLE 5

Use of Aqueous Ethanol with Triglycerides

Crude monoglycerides (IV 70) were weighed into graduated tubes and aqueous ethanol was added (16 vol %, 23 vol The result for 60% water in the aqueous ethanol is from a separate experiment. Water loadings higher than 50 vol % in ethanol tended to produce systems with more than two phases.

The results show the generally favorable characteristics of the aqueous ethanol/triglyceride system. For a given charge, increasing water content resulted in an increased selectivity but decreased extraction coefficient. For a given water content, the selectivity decreases with increased monoglyceride charge. This factor supports the need for a washing section if high loadings are to be used.

TABLE A

| Water in ETOH (vol %) | Charge (g crude) in 10 ml sol | Phase ratio (vol polar/non-polar) | Phase fat content (g/ml) non-polar | Phase fat content (g/ml) polar | [MG] polar (%) | [DG] polar (%) | [TG] polar (%) | [MG] non-polar (%) | [DG] non-polar (%) | [TG] non-polar (%) | Selectivity MG/DG | Kmono |
|---|---|---|---|---|---|---|---|---|---|---|---|---|
| 16 | 10 | 3 | 0.112 | 0.706 | 81.2 | 14.6 | 4.2 | 5.4 | 12.7 | 81.9 | 13.1 | 2.39 |
| 16 | 10 | 3 | 0.082 | 0.729 | 84.6 | 12.8 | 2.6 | 3.8 | 10.2 | 86 | 17.7 | 2.50 |
| 30 | 10 | 3 | 0.074 | 0.887 | 93.4 | 6.6 | 0.0 | 7.4 | 12.5 | 80.1 | 23.9 | 1.05 |
| 30 | 10 | 3 | 0.055 | 0.769 | 92.6 | 7.4 | 0.0 | 6.7 | 12.3 | 81 | 23.0 | 0.99 |
| 16 | 20 | 3 | 0.194 | 0.759 | 76.0 | 16.7 | 7.3 | 9.2 | 16.5 | 74.3 | 8.2 | 2.11 |
| 16 | 20 | 3 | 0.224 | 0.650 | 69.2 | 20.0 | 10.8 | 8.9 | 13.5 | 77.6 | 5.2 | 2.68 |
| 30 | 20 | 3 | 0.151 | 0.748 | 79.6 | 14.8 | 5.6 | 9.6 | 15.8 | 74.6 | 8.9 | 1.68 |
| 30 | 20 | 3 | 0.116 | 0.774 | 86.3 | 10.6 | 3.1 | 12.2 | 16.6 | 71.2 | 11.1 | 1.06 |
| 16 | 15 | 2 | 0.107 | 0.739 | 80.0 | 15.1 | 4.9 | 5.7 | 12 | 82.2 | 11.2 | 2.03 |
| 16 | 15 | 2 | 0.132 | 0.818 | 77.4 | 17.9 | 4.7 | 5.3 | 11.3 | 83.4 | 9.2 | 2.36 |
| 16 | 15 | 4 | 0.098 | 0.823 | 76.4 | 19.5 | 4.1 | 7.8 | 13.3 | 78.8 | 6.7 | 1.17 |
| 16 | 15 | 4 | 0.108 | 0.763 | 75.0 | 20.9 | 4.0 | 6.1 | 12.2 | 81.7 | 7.2 | 1.70 |
| 30 | 15 | 2 | 0.071 | 0.833 | 90.5 | 9.5 | 0.0 | 9.6 | 11.2 | 79.2 | 11.1 | 0.80 |
| 30 | 15 | 2 | 0.069 | 0.888 | 90.9 | 9.1 | 0.0 | 9.2 | 11.1 | 79.7 | 12.1 | 0.76 |
| 30 | 15 | 4 | 0.065 | 0.705 | 88.9 | 11.1 | 0.0 | 9.7 | 15 | 75.3 | 12.4 | 0.84 |
| 23 | 10 | 2 | 0.049 | 0.729 | 88.6 | 11.4 | 0.0 | 5.8 | 7.6 | 86.6 | 10.2 | 1.02 |
| 23 | 10 | 2 | 0.070 | 0.724 | 87.8 | 10.6 | 1.6 | 5.8 | 7.9 | 86.2 | 11.3 | 1.46 |
| 23 | 20 | 2 | 0.112 | 0.778 | 86.6 | 13.4 | 0.0 | 10.5 | 12.9 | 76.5 | 7.9 | 1.18 |
| 23 | 20 | 2 | 0.136 | 0.717 | 82.1 | 14.4 | 3.6 | 11.0 | 13.3 | 75.7 | 6.9 | 1.42 |
| 23 | 10 | 4 | 0.058 | 0.880 | 86.7 | 10.4 | 2.9 | 7.7 | 12.1 | 80.2 | 13.1 | 1.0 |
| 23 | 10 | 4 | 0.088 | 0.500 | 84.6 | 9.2 | 6.2 | 4.9 | 11.2 | 83.9 | 21.0 | 2.35 |
| 23 | 20 | 4 | 0.139 | 0.553 | 79.2 | 14.3 | 6.5 | 14.3 | 18.2 | 67.5 | 7.0 | 1.39 |
| 23 | 20 | 4 | 0.127 | 0.691 | 84.9 | 13.5 | 1.6 | 8.4 | 17.5 | 74.1 | 13.1 | 1.85 |
| 23 | 15 | 3 | 0.098 | 0.784 | 90.3 | 9.7 | 0.0 | 7.9 | 11.6 | 80.4 | 13.7 | 1.43 |
| 23 | 15 | 3 | 0.111 | 0.683 | 89.9 | 10.1 | 0.0 | 10.3 | 14.9 | 74.8 | 12.9 | 1.42 |
| 23 | 15 | 3 | 0.102 | 0.893 | 89.6 | 10.4 | 0.0 | 10.0 | 12.6 | 77.4 | 10.9 | 1.03 |
| 23 | 15 | 3 | 0.091 | 0.661 | 92.5 | 7.5 | 0.0 | 7.4 | 14.2 | 78.4 | 23.7 | 1.73 |
| 23 | 15 | 3 | 0.094 | 0.738 | 92.3 | 7.7 | 0.0 | 8.5 | 14.1 | 77.5 | 19.9 | 1.38 |
| 23 | 15 | 3 | 0.099 | 0.768 | 92.3 | 7.7 | 0.0 | 10.6 | 13.9 | 75.5 | 15.7 | 1.12 |

EXAMPLE 6

Equilibrium Distribution at Low Diglyceride Level

A series of experiments was run to determine the equilibrium distribution between mono-, di-, and triglycerides at moderate levels of diglyceride. Mixtures were made up using a triglyceride oil, distilled monoglycerides (IV 70), and aqueous ethanol. The aqueous ethanol was either 16, 23, or 30 vol % water in ethanol. The aqueous ethanol was added in an amount sufficient to give a two phase system. The samples were mixed and equilibrated at about 65° C. Aliquots were removed and the fat content determined by residual weight after evaporation at about 110° C. in flowing nitrogen. The evaporated samples were then derivitized and analyzed by GC to determine the monoglyceride, diglyceride, and triglyceride content. Water was determined by Karl Fisher analysis and found to be about 0–3 wt % of the less polar phase. The ethanol in the less polar phase increased with increasing monoglyceride content. Selectivity of the polar phase for monoglycerides over diglycerides and the monoglyceride extraction factor (concentrations based on weight) are shown in the attached Table B.

This example shows that as the fat content of the polar phase increases (increased loading) the amount of triglycerides entering the polar phase also increases, eventually limiting the monoglyceride purity. However, even at fat contents of greater than 10 wt % in the polar phase, the triglycerides are relatively low for the aqueous ethanol/triglyceride system.

TABLE B

| Polar phase MG (wt %) | Polar phase DG (wt %) | Polar phase TG (wt %) | Nonpolar phase MG (wt %) | Nonpolar phase DG (wt %) | Nonpolar phase TG (wt %) | Fat content polar phase, Wt % | Fat content less polar phase, Wt % | Selectivity MG/DG | K (mono) wt basis |
|---|---|---|---|---|---|---|---|---|---|
| 23% Water | | | | | | | | | |
| 95.85 | 1.21 | 2.95 | 0.67 | 1.39 | 97.95 | 3 | 99 | 164.3 | 4.34 |
| 96.15 | 0.43 | 3.41 | 2.29 | 1.27 | 96.44 | 2 | 98 | 124.0 | 0.86 |
| 96.82 | 0.79 | 2.39 | 3.27 | 1.31 | 95.42 | 10 | 97 | 49.1 | 3.05 |
| 98.38 | 0.44 | 1.18 | 4.15 | 1.32 | 94.52 | 5 | 99 | 71.1 | 1.20 |
| 96.86 | 0.95 | 2.18 | 5.29 | 1.62 | 93.09 | 11 | 96 | 31.2 | 2.10 |
| 94.2 | 0.45 | 5.35 | 10.15 | 1.05 | 88.8 | 14 | 96 | 21.7 | 1.35 |
| 88.32 | 1.05 | 10.63 | 13.07 | 1.21 | 85.72 | 25 | 95 | 7.8 | 1.78 |

TABLE B-continued

| Polar phase MG (wt %) | Polar phase DG (wt %) | Polar phase TG (wt %) | Nonpolar phase MG (wt %) | Nonpolar phase DG (wt %) | Nonpolar phase TG (wt %) | Fat content polar phase, Wt % | Fat content less polar phase, Wt % | Selectivity MG/DG | K (mono) wt basis |
|---|---|---|---|---|---|---|---|---|---|
| 88.62 | 1.22 | 10.15 | 11.02 | 1.33 | 87.65 | 21 | 96 | 8.8 | 1.78 |
| 92.4 | 1.18 | 6.42 | 18.63 | 1.31 | 80.06 | 15 | 94 | 5.5 | 0.79 |
| 30% Water | | | | | | | | | |
| 94.79 | 0.66 | 4.56 | 2.02 | 1.46 | 96.52 | 6 | 98 | 103.8 | 2.87 |
| 96.94 | 0.98 | 2.08 | 3.31 | 1.22 | 95.48 | 8 | 98 | 36.5 | 2.39 |
| 87.48 | 0.65 | 11.87 | 6.2 | 1.48 | 92.32 | 8 | 98 | 32.1 | 1.15 |
| 98.66 | 0.45 | 0.89 | 6.72 | 1.41 | 91.87 | 5 | 96 | 46.0 | 0.76 |
| 97.32 | 0.66 | 2.01 | 7.4 | 1.53 | 91.07 | 8 | 94 | 30.5 | 1.12 |
| 95.36 | 0.79 | 3.85 | 10.25 | 1.65 | 88.1 | 13 | 93 | 19.4 | 1.30 |
| 94.78 | 1.16 | 4.06 | 13.89 | 1.81 | 84.3 | 9 | 95 | 10.6 | 0.65 |
| 91.7 | 1.28 | 7.02 | 13.47 | 1.71 | 84.83 | 17 | 95 | 9.1 | 1.22 |
| 94.26 | 1.36 | 4.38 | 43.4 | 1.76 | 54.85 | 14 | 64 | 2.8 | 0.48 |
| 16% Water | | | | | | | | | |
| 95.1 | 0.51 | 4.39 | 1.98 | 1.18 | 96.83 | 3 | 97 | 111.1 | 1.49 |
| 98 | 0.56 | 1.42 | 3.73 | 1.3 | 94.97 | 7 | 98 | 61.0 | 1.88 |
| 96.2 | 0.82 | 2.96 | 5.4 | 1.37 | 93.23 | 20 | 96 | 29.8 | 3.71 |
| 90.7 | 1.11 | 8.16 | 7.36 | 1.37 | 91.27 | 9 | 95 | 15.2 | 1.17y |
| 88.6 | 1.12 | 10.23 | 7.99 | 1.47 | 90.54 | 21 | 94 | 14.6 | 2.48 |
| 88.4 | 1.18 | 10.45 | 14.82 | 1.56 | 83.62 | 21 | 92 | 7.9 | 1.36 |
| 84.2 | 1.27 | 14.57 | 19.03 | 1.63 | 79.34 | 24 | 90 | 5.7 | 1.18 |
| 83 | 1.42 | 15.59 | 24.68 | 1.73 | 73.69 | 26 | 88 | 4.1 | 0.99 |
| 80.7 | 1.44 | 17.85 | 25.38 | 1.83 | 72.59 | 29 | 86 | 4.0 | 1.07 |

EXAMPLE 7

Equilibrium Distribution at Moderate Diglyceride Level

A series of experiments was run to determine the equilibrium distribution between mono-, di-, and triglycerides at moderate levels of diglyceride. Mixtures were made up using a previously extracted triglyceride oil/crude monoglyceride mixture (to provide a low level of monoglycerides and moderate level of diglycerides), distilled monoglycerides (IV 70), and aqueous ethanol. The aqueous ethanol was 23 vol % water in ethanol. The aqueous ethanol was added in an amount sufficient to give a two phase system. The samples were mixed and equilibrated at about 65° C. Aliquots were removed and the fat content determined by residual weight after evaporation in a vacuum oven at about 120° C. The evaporated samples were then derivitized and analyzed by GC to determine the monoglyceride, diglyceride, and triglyceride content. Water was determined by Karl Fisher analysis and found to be about 0–3 wt % of the less polar phase. Ethanol, determined by difference, was found to be 8–5 wt % of the less polar phase. The ethanol in the less polar phase increased with increasing monoglyceride content. Selectivity of the polar phase for monoglycerides over diglycerides and the monoglyceride extraction factor (concentrations based on weight) are shown in the attached Table C. These data can be used to assist in the design of a liquid-liquid extraction process.

TABLE C

| Grams Comp. #1 | Grams Comp. #2 | Grams Comp. #3 | wt % MG polar phase | wt % DG polar phase | wt % TG polar phase | wt % MG less polar phase | wt % DG less polar phase | wt % TG less polar phase | Fat content Polar phase wt % | Fat content wt %, less polar phase | [1]Selectivity | [2]K (mono) wt basis |
|---|---|---|---|---|---|---|---|---|---|---|---|---|
| 85.11 | 0.00 | 25.13 | 92.9 | 5.7 | 1.4 | 4.5 | 11.7 | 83.8 | 6.29 | 91.33 | 42.4 | 1.42 |
| 81.91 | 1.64 | 24.76 | 90.6 | 7.2 | 2.2 | 5.1 | 11.8 | 83.1 | 10.10 | 90.38 | 29.1 | 1.99 |
| 82.99 | 9.97 | 26.31 | 79.5 | 10.0 | 10.5 | 10.6 | 10.8 | 78.6 | 28.61 | 88.2 | 5.1 | 2.43 |
| 83.81 | 19.21 | 32.50 | 67.3 | 10.3 | 22.4 | 15.6 | 9.2 | 75.2 | 40.97 | 63.68 | 3.9 | 2.11 |
| 86.27 | 27.62 | 51.36 | 67.1 | 10.1 | 22.8 | 15.9 | 9.6 | 74.5 | 41.15 | 83.97 | 4.0 | 2.07 |
| 82.32 | 34.74 | 56.01 | 57.9 | 9.7 | 32.3 | 18.6 | 9.1 | 72.4 | 48.87 | 82.21 | 2.9 | 1.85 |
| 84.78 | 48.03 | 80.32 | 60.0 | 8.9 | 31.1 | 17.6 | 7.3 | 75 | 47.64 | 83 | 2.8 | 1.96 |

Component #1 is a mixture of 8 wt % monoglycerides, 13 wt % diglycerides, and 79% triglycerides
Component #2 is distilled monoglycerides, used to adjust overall composition
Component #3 is aqueous ethanol, 23 vol % water in ethanol

EXAMPLE 8

Extraction of IV 2 Crude Monoglycerides Using Triglyceride and Aqueous Ethanol A single stage separation was performed by mixing 10 g of crude glycerol monostearate (IV approximately 2, roughly 70 wt % monoglyceride and 30 wt % diglyceride) with 30 grams of a polar solvent (10 g water, 20 g ethanol) and 10 grams of a triglyceride oil (fully hydrogenated soybean oil, IV less than about 5) at 70° C. and allowing the mixture to separate into two phases. Phase 1 weighed 34.7 g and had a fat content of 14.7 wt %, with composition 77.4 wt % monoglyceride, and 10.5 wt % diglyceride, and 11.9 wt % triglyceride. Phase 2 weighed 15.2 grams and had a fat content of 84.8 wt %, with a composition of 12.9 wt % monoglyceride, 17.2 wt % diglyceride, and 70 wt % triglyceride. These results indicate a selectivity for the monoglyceride over diglyceride to the polar phase of 9.8 and an extraction factor for the monoglycerides to the polar phase of 1.04, on a weight basis. The less polar phase was found to contain 2.5 wt % water, and, by difference, 12.7 wt % ethanol.

This experiment shows the general feasibility of purification of low IV monoglycerides using a low IV fat.

EXAMPLE 9

Use of Multiple Triglyceride 'Wash' Extractions in Combination with Aqueous Ethanol A four-stage batch extraction was performed by mixing 100 g crude monoglyceride (IV 70) with 200 g ethanol and 93 g water at about 70° C. and sequentially treating with 114 g aliquots of triglyceride oil (IV 40). Approximately 4–5 g of the polar phase was removed for analysis after each extraction. Fresh triglyceride oil was used for each extraction. Samples of the polar phase and less polar phase were analyzed for water content (Karl Fisher), fat content (evaporation residue), and ethanol (by difference). The evaporated samples were then derivitized and analyzed by GC for the monoglyceride, diglyceride, and triglyceride content. Results are shown in Table D below.

This example shows the progressive removal of diglycerides from monoglycerides, by washing with triglycerides.

EXAMPLE 10

Comparative Analysis of Distilled Monoglycerides

Several samples of commercially available distilled monoglycerides were analyzed by gas chromatography to determine the monoglyceride, diglyceride, and triglyceride content (excluding glycerol, free fatty acid, and other contaminants). The results, shown in Table E below, indicate that diglycerides are the major impurity in the monoglycerides and are present at levels of greater than 2.9 wt %.

TABLE E

| Sample ID | Monoglyceride wt % | Diglyceride wt % | Triglyceride wt % |
|---|---|---|---|
| AI90NLK | 95.01 | 3.88 | 1.11 |
| AI90AB | 96.12 | 3.13 | .075 |
| AI90PBK | 93.32 | 5.35 | 1.33 |
| AI90SBK | 96.43 | 2.91 | 0.65 |
| AI IV 70 | 96.19 | 3.63 | 0.18 |
| Danisco IV 40 | 96.99 | 3.01 | 0 |
| AI90VCK | 96.99 | 3.01 | 0 |
| AI Starplex 90 | 96.68 | 3.11 | 0.21 |

EXAMPLE 11

Washing of Raffinate to Reduce Alcohol Content

A sample of raffinate was prepared by doing a single extraction of crude monoglycerides (1000 g, IV 70) with a triglyceride mix of 500 g IV 2 soybean oil and 500 g IV 70 soybean oil and an aqueous alcohol mix of 930 g distilled water and 2000 g food grade ethanol. After equilibration at 70° C., the phases were separated and the raffinate was divided into 10 gram aliquots. The aliquots were held at 70° C. and treated as shown in Table F. The treatment reduced the ethanol content of the raffinate, as shown in Table F. Fat content was determined by evaporation residue, water by Karl Fischer, and ethanol by difference.

TABLE D

| Phase | Water, wt % | Ethanol, wt % | Fat, wt % | Mono-glyceride, wt % | Di-glyceride, wt % | Tri-glyceride, wt % |
|---|---|---|---|---|---|---|
| Stage 1, polar | 27.1 | 59.4 | 13.5 | 83.7 | 10.7 | 5.6 |
| Stage 2, polar | 29.1 | 62.1 | 8.8 | 94.1 | 2.6 | 3.3 |
| Stage 3, polar | 25.9 | 63.6 | 10.5 | 85.8 | 1 | 13.2 |
| Stage 4, polar | 31.1 | 62.7 | 6.2 | 87.1 | 0.7 | 12.2 |
| Stage 1, less polar | 2.6 | 10.4 | 87 | 14.6 | 18.4 | 67 |
| Stage 2, less polar | 2.1 | 11.9 | 86 | 6.7 | 4.4 | 88.9 |
| Stage 3, less polar | 2.3 | 9.7 | 88 | 6.3 | 1.7 | 92 |
| Stage 4, less polar | 5.3 | 17.7 | 77 | 6.4 | 1.5 | 92.1 |

Applicants believe that additional washing stages, or a counter current extraction apparatus, could be used to reduce the diglyceride content of the polar phase to any desirable level. Applicants also believe that the triglyceride content of the polar phase can be controlled through choice of the aqueous alcohol, contacting, temperature, overall fat content, or other methods.

TABLE F

|  | Raffinate before washing | Raffinate washed 3 times, 4 ml water | Raffinate washed 2 times, 12 ml water | Raffinate, washed 1 time, 25 ml water |
|---|---|---|---|---|
| Fat content, wt % | 88.3 | 96 | 96.3 | 92.4 |
| Water, wt % | 2.4 | 2 | 1.6 | 1.9 |
| Ethanol, wt % | 9.3 | 2 | 2.1 | 5.7 |

This example shown the ability to wash the raffinate by contacting with water, to reduce the alcohol content.

EXAMPLE 12

Product Recovery in a Wiped Film Evaporator

The aqueous alcohol/monoglyceride extract from extraction of crude monoglycerides of animal origin (62 wt % monoglyceride, 35 wt % diglyceride, and 3 wt % triglyceride) was pre-concentrated using a rotary evaporator to a fat content of about 44 wt %. This material was then fed at 170 g/hr to a lab scale wiped film evaporator, Model KDL-4 from UIC, Inc., Joliet, Ill., running at an evaporator temperature of 76° C. and a pressure of 250 mm HG absolute. The bottoms product was collected and volatiles were determined by evaporation at 110° C. in flowing nitrogen. The residual volatiles, water and ethanol, were less than 0.4 wt %.

EXAMPLE 13

GC Analytical Procedure

Fat compositions can be determined by any suitable method, for example gas chromatography. A preferred method is to evaporate the samples at approximately 110° C. in flowing nitrogen, or under vacuum, to remove water and alcohol. Approximately 0.4 g of sample is then dissolved in 400 microliter of chloroform and derivitized by adding 400 microliter of pyridine and 200 microliter of BSTFA solution from Regis Technologies, Inc., Morton Grove, Ill. (BSTFA is Bis(trimethylsilyl)trifluoroacetamide). The sample is then analyzed using a Hewlett Packard Model 5890 using a 1 meter capillary column, Model DB5HT from J&W. The sample is prepared for GC injection by diluting 10 microliters of the derivitized solution with 1.5 ml of dry chloroform prior to injection. The area percent figures are converted to weight percent for the monoglycerides, diglycerides, and triglycerides using relative response factors determined from appropriate standards. The totals are normalized to 100% for the combined mono-, di-, and triglycerides.

A Hypothetical Commercial System

A commercial plant, with a capacity of about 20 million pounds of purified monoglyceride per year, could theoretically be set up with the following flow rates. A triglyceride rich stream, with a flow rate of about 2165 lb/hr triglyceride, and other components as described in the wash extraction section, would be mixed with a crude monoglyceride stream which has a flow rate of 3900 lb/hr, consisting of 2400 lb/hr of monoglyceride, 1350 lb/hr diglyceride, and 150 lb/hr of triglyceride. The crude monogloycerides would be prepared by the reaction of diglycerides, triglycerides, and glycerin using a catalyst, such as NaOH or other bases. After the reaction, the catalyst would be neutralized and removed and the crude monoglycerides cooled. Excess glycerin would be decanted off and an evaporator would be used to further strip glycerin from the product. The combined stream (crude monoglycerides and triglyceride rich stream) would be charged to one end of a countercurrent extraction train, consisting of about 4 mixer/settler vessels. This extraction train would be known as the primary extraction train. To the other end of the extraction train would be charged 14,630 lb/hr of an aqueous alcohol extractant, consisting of 10,850 lb/hr of ethanol and 3,780 lb/hr water. The raffinate phase, following extraction, would contain about 2115 lb/hr triglyceride, 1330 lb/hr diglyceride, 20 lb/hr monoglyceride, 80 lb/hr water, and 350 lb/hr ethanol. The raffinate stream would be contacted countercurrently with 700 lb/hr of water, to form an aqueous phase with 700 lb/hr water and 270 lb/hr of ethanol, which would be used as a portion of the aqueous alcohol extractant composition. The raffinate would then be vacuum stripped to remove ethanol and water and would be used as a feedstock to a monoglyceride production reactor.

The extractant phase, following the extraction train, would contain approximately 10,850 lb/hr ethanol, 3,780 lb/hr water, 2,400 lb/hr monoglyceride, 350 lb/hr diglyceride, and 200 lb/hr triglyceride. This phase would be fed to one end of a countercurrent extraction train, containing another 4 mixer/settler stages. This extraction train would be used to "wash" the diglycerides from the aqueous alcohol extractant phase to further purify the monoglycerides. To the other end of the train would be fed about 2065 lb/hr of triglyceride. After extraction, the triglyceride rich stream would have a flow rate of about 2165 lb/hr of triglyceride, 330 lb/hr of diglyceride, 20 lb/hr of monoglyceride, 80 lb/hr water, and 350 lb/hr ethanol. It would preferably be used as the triglyceride rich stream feed to the primary extraction train, described above. The extractant phase, following the wash extraction stage, would have a flow rate of about 10,500 lb/hr ethanol, 3700 lb/hr water, 2380 lb/hr monoglyceride, 20 lb/hr diglyceride and 100 lb/hr triglyceride.

The purified monoglycerides would be removed from the extractant stream. For example, a multiple stage evaporator, perhaps followed by a wiped film evaporator, would be used to remove the ethanol and water to produce a stream of molten monoglycerides, containing approximately 2380 lb/hr monoglyceride, 20 lb/hr diglyceride, and 100 lb/hr triglyceride.

Use of Purified Monoglycerides or Purified PGME

Purified monoesters can be used to prepare a liquid shortening, suitable for use in bread, cake batter, pizza dough, and other applications. The liquid shortening would consist of up to about 12 wt % purified monoester, about 2–8 wt % of a solid fat with IV less than about 6, and the remainder would primarily be a liquid oil, such as partially hydrogenated vegetable oil with an IV of about 90 to 140.

Purified monoesters can also be used to prepare a plastic shortening, suitable for use in cake mixes, and would contain about 2–14 wt % of the purified monoester (typically PGME). For bread shortenings, the level of monoester would be higher, amounting to about 6–20 wt % of the shortening, to achieve a total level in the bread of about 0.2–2.5 wt % monoester.

Purified monoglycerides can also be added directly to bakery products. Typically the monoglyceride would be added at a rate of 0.2–0.5 wt %, dry, based on flour. The monoglyceride would typically be hydrated prior to use.

Purified monoglycerides, typically with IV less than about 5, could also be added directly to starch-based foods and dried potato products. The use level would typically be 0.1–1.5 wt %.

Purified PGME, with an IV less than about 5, can also be used in whipped toppings, with a use level typically of 0.5–2 wt %, and in powdered toppings at levels of 5–10 wt %.

The purified monoglycerides are also suitable for use in making margarine. For example, a stick margarine or whipped hard margarine can be made using about 0.1–0.5 wt % of purified monoglyceride (IV less than about 5), about 80 wt % vegetable fat (may be partially hydrogenated), about 17% water or milk, and salt, vitamins, flavor, color, antioxidants, other emulsifiers, etc. A soft margarine (tub margarine) could be made in a similar manner, but the monoglyceride level would preferably be increased slightly and the IV of the monoglyceride would typically be about 30–70. The vegetable fat would be largely replaced with a partially hydrogenated vegetable oil to provide the desired degree of softness. A liquid margarine would use a monoglyceride with an IV of 70–125 and would replace the vegetable fat with a liquid vegetable oil with just a few percent of hard fat dispersed in it (a liquid shortening).

Diet table spreads can be made using 40–75 wt % of a vegetable fat (may be partially hydrogenated), 23–58 wt % water, 0.5–1.5 wt % purified monoglyceride (IV typically 70–125), and salt, vitamins, flavor, color, antioxidants, other emulsifiers, etc. As the amount of fat is reduced the amount of monoglyceride is increased. For spreads with less than 40% fat, the monoglyceride content would typically be 1–2 wt, and for fat-free spreads the monoglyceride content would typically be about 2–4 wt %.

The purified monoesters, when combined with other additives, are also suitable for ice cream production.

IX. Some Variations

It is anticipated that in some applications variations of the techniques described herein will be desirable. For example, if the triglycerides content of the polar phase of leaving the washing step, for example in line 66, FIG. 1, is undesirably high, steps can be taken to lower its content before the monoglycerides are purified or isolated. This can be done, for example, by increasing the water content, rendering the triglycerides less soluble in the polar phase. In addition, a non-polar solvent, such as a hydrocarbon solvent, could be used to facilitate this. It is noted that in general it is preferred to avoid hydrocarbon solvents in systems according to the present invention but they may find some use in such instances.

As an alternative to the approach described in the previous paragraph, one could include hydrocarbon solvents in the triglycerides feed in line 65, FIG. 1, going into the washing step 60. Generally, it is anticipated that if this is practiced, this system would involve less than 20% by weight hydrocarbon solvent, and typically 10% by weight or less, based on total weight of triglycerides plus hydrocarbon, i.e. non-polar solvent. It is foreseen that the addition of hydrocarbon solvents will not be preferred, since steps would need to be taken to handle their removal. However, they may be useful to facilitate some liquid/liquid extractions in systems according to the present invention.

Also, in some options one may wish to add water or alcohol to the polar phase as it leaves the extraction step and prior to the washing step, for example, addition to line 55, FIG. 1. This would be done in order to modify the polarity of the phase, thereby affecting the solubility of diglycerides and/or triglycerides therein, during the washing step.

It is also noted that in some systems mixed alcohols may be desirable, as the alcohol solvent in the alcohol phase. This might be usable to fine tune the selectivities in some systems, for example.

In some systems, it may be desirable to conduct both the primary extraction and the follow up washing in the same multi-stage extraction equipment. In such systems, the crude monoglyceride feed would occur at an intermediate location.

What is claimed is:

1. A method of preparing a purified monoester composition from a crude monoester composition, said method including steps of:
   (a) providing a crude monoester composition including at least one monoester of a fatty acid selected from the group consisting of: $C_3$-diol monoesters of fatty acids and $C_3$-triol monoesters of fatty acids;
   (b) adding, to the crude monoester composition, an effective amount of triglycerides to form a primary extraction, triglyceride-containing, phase; and,
   (c) extracting monoester from the primary extraction, triglyceride-containing phase with an extractant, by liquid-liquid extraction.

2. A method according to claim 1 including:
   (a) conducting said step of extracting monoester from the triglyceride-containing phase with an alcohol/water extractant;
   (b) separating an alcohol/water extractant phase from a resulting primary extraction, triglyceride-containing phase, after conducting the extracting of step 1(c); and,
   (c) isolating a purified monoester composition from the alcohol/water extractant phase after said step of separating.

3. A method according to claim 2 wherein:
   (a) said step of providing a crude monoester composition comprises providing a crude monoglyceride composition.

4. A method according to claim 3 wherein:
   (a) said step of providing a crude monoglyceride composition includes providing a composition including at least 30% monoglyceride and at least 25% diglyceride, by weight, based on a total weight of monoglycerides, diglycerides and triglycerides in the crude monoglyceride composition.

5. A method according to claim 4 wherein:
   (a) said step of providing a crude monoglyceride composition includes providing a composition containing no more than 70% monoglycerides, by weight, based on a total weight of monoglycerides, diglycerides and triglycerides in the crude monoglyceride composition; and,
   (b) said method is conducted to isolate a purified monoester composition, from step 2(c), having a monoglyceride presence of no less than 85%, based on a total weight of monoglycerides, diglycerides and triglycerides in the purified monoester composition.

6. A method according to claim 3 wherein:
   (a) said step of providing a crude monoglyceride composition comprises providing a crude monoglyceride composition prepared from reacting a naturally occurring triglyceride composition with glycerol.

7. A method according to claim 6 wherein:
   (a) said step of providing a crude monoglyceride composition comprises providing a crude monoglyceride composition prepared from reacting glycerol with oil selected from the group consisting of: palm oil; sunflower oil; canola oil; and, soybean oil.

8. A method according to claim 3 wherein:
   (a) said step of extracting with alcohol/water extractant comprises extracting with an ethanol/water extractant.

9. A method according to claim 8 wherein:
   (a) said step of extracting with ethanol/water extractant comprises extracting with extractant containing: 60% to 90% ethanol, by weight; and, 10% to 40% water, by weight.

10. A method according to claim 8 wherein:
(a) said step of extracting with ethanol/water extractant comprises conducting a multi-stage, counter-current extraction.

11. A method according to claim 3 including a step of:
(a) washing the alcohol/water extractant phase with a triglyceride-containing phase, after said step of separating and prior to said step of isolating.

12. A method according to claim 11 wherein:
(a) said step of washing comprises conducting a multi-stage, counter-current, wash.

13. A method according to claim 11 wherein:
(a) said step of adding an effective amount of triglyceride to the crude monoester composition comprises adding, as the triglyceride, a triglyceride-containing phase from said step of washing.

14. A method according to claim 2 wherein:
(a) said step of providing crude monoester composition comprises providing, prior to said step of triglyceride addition, a crude monoester composition comprising no more than 20% triglycerides, by weight, based on total weight of monoglycerides, diglycerides and triglycerides in the crude monoester composition.

15. A method according to claim 2 wherein:
(a) said step of providing a crude monoester composition comprises providing a crude monoglyceride composition comprising no more than 70% monoglycerides, by weight, based on a total weight of monoglycerides, diglycerides and triglycerides in the crude monoglyceride composition; and,
(b) said method is conducted to isolate a purified monoester composition, from step 2(c) having: a monoglyceride presence of no less than 85%, based on a total weight of monoglycerides, diglycerides and triglycerides in the purified monoester composition; and, a diglyceride to triglyceride weight ratio, in the purified monoester composition, of no greater than 1:1.

16. A method according to claim 1 wherein:
(a) said step of providing a crude monoester composition comprises providing a crude propylene glycol monoester composition.

17. A method for preparing a purified monoglyceride, said method including a step of:
(a) extracting monoglycerides, with an extractant, from a mixture of monoglycerides, diglycerides and triglycerides under conditions providing:
(i) a selectivity of monoglycerides relative to diglycerides of at least 5; and,
(ii) a monoglycerides load, in the extractant, of at least 10 g monoglyceride per 100 g extractant.

18. A method according to claim 17 including a step of:
(a) washing a resulting extractant, containing monoglycerides, from the step of extracting, with a triglyceride-containing phase.

19. A method according to claim 18 wherein:
(a) said step of washing comprises a multi-stage wash.

20. A method according to claim 18 wherein:
(a) said step of extracting comprises a multi-stage extraction.

21. A method according to claim 18 wherein:
(a) said triglyceride-containing phase, prior to use in washing, contains at least 80% triglycerides, by weight, based on total weight of the triglyceride-containing phase.

22. A method according to claim 18 wherein:
(a) said step of extracting comprises extracting from a mixture having a composition wherein, prior to extraction:
(i) a diglyceride presence was less than a triglyceride presence, by weight; and,
(ii) a diglyceride presence was less than 2 times a monoglyceride presence, by weight.

23. A method according to claim 22 wherein:
(a) said step of extracting comprises extracting from a crude mixture having a monoglyceride presence, by weight, prior to said step of extracting no greater than about 60%, based on total weight of monoglycerides, diglycerides and triglycerides; and,
(b) said step of extracting is conducted to provide, in the extractant, a monoglycerides presence of at least 70% by weight, based on total weight of monoglycerides, diglycerides and triglycerides in the extractant.

24. A method of purifying monoglycerides comprising a step of:
(a) washing an alcohol/water phase having monoglycerides and diglycerides therein, with a triglyceride mixture.

25. A method for preparing a purified monoglyceride from a mixture including monoglycerides, diglycerides, and triglycerides, the method including a step of:
(a) extracting monoglycerides, with a liquid extractant, from a mixture having a composition, prior to extraction, containing:
(i) a diglyceride presence of less than a triglyceride presence, by weight;
(ii) a diglyceride presence of no more than 2 times a monoglyceride presence, by weight; and,
(iii) a triglyceride presence of at least 30%, by weight, based on total weight of monoglycerides, triglycerides and diglycerides in the mixture.

26. A purified monoglyceride composition comprising:
(a) at least 85%, by weight, monoglycerides, based on a total weight of monoglycerides, diglycerides and triglycerides; and,
(b) a weight ratio of diglyceride to triglyceride of no greater than 1:1.

27. A purified monoglyceride composition according to claim 26 having:
(a) at least 2%, by weight, based on total weight of monoglycerides, diglycerides and triglycerides, of diglycerides and triglycerides added together.

28. A purified monoglyceride composition according to claim 26 wherein:
(a) the weight ratio of diglyceride to triglyceride is less than 1:3.

29. A purified monoglyceride composition according to claim 26 comprising:
(a) a monoglyceride which has been purified from a crude mixture of monoglyceride, diglyceride and triglyceride, without a step of distilling monoglyceride.

* * * * *

UNITED STATES PATENT AND TRADEMARK OFFICE
CERTIFICATE OF CORRECTION

PATENT NO. : 5,859,270

DATED : JANUARY 12, 1999

INVENTOR(S) : KOLSTAD ET AL.

It is certified that error appears in the above-identified patent and that said Letters Patent is hereby corrected as shown below:

Col. 30, Table C, column "Selectivity", third line down: "5.1" should read —8.1—

Signed and Sealed this

Twenty-fourth Day of October, 2000

*Attest:*

Q. TODD DICKINSON

*Attesting Officer*      *Director of Patents and Trademarks*